(12) United States Patent
Karaplis et al.

(10) Patent No.: US 7,393,837 B2
(45) Date of Patent: Jul. 1, 2008

(54) INHIBITION OF PEX IN THE TREATMENT OF METABOLIC BONE DISEASES

(75) Inventors: Andrew C. Karaplis, Kirkland (CA); David Goltzman, Westmount (CA); Mark L. Lipman, Town of Mount Royal (CA); Janet E. Henderson, Montreal West (CA)

(73) Assignee: McGill University, Montreal (CA)

( * ) Notice: Subject to any disclaimer, the term of this patent is extended or adjusted under 35 U.S.C. 154(b) by 406 days.

(21) Appl. No.: 10/952,878

(22) Filed: Sep. 30, 2004

(65) Prior Publication Data

US 2005/0113303 A1 May 26, 2005

Related U.S. Application Data

(63) Continuation-in-part of application No. 09/806,110, filed as application No. PCT/CA99/00895 on Sep. 27, 1999, now abandoned.

(30) Foreign Application Priority Data

Sep. 28, 1998 (CA) .................................. 2245903

(51) Int. Cl.
A61K 13/7028 (2006.01)
A61K 5/19 (2006.01)
(52) U.S. Cl. ................................ 514/25; 514/31; 514/2
(58) Field of Classification Search .................. 514/12, 514/25, 292
See application file for complete search history.

(56) References Cited

U.S. PATENT DOCUMENTS 6,583,114 B2   6/2003   Vickery

FOREIGN PATENT DOCUMENTS

| CA | 2264655 | 3/1998 |
|---|---|---|
| WO | WO-96/19246 | 6/1996 |
| WO | WO 97/37967 A1 | 10/1997 |
| WO | WO-98/10078 | 3/1998 |
| WO | WO03/030956 | * 4/2003 |

OTHER PUBLICATIONS

2006 Chemical Abstracts Catalog, published 2006 by Chemical Abstracts Service, p. 52.*
Dolan et al., "The Cost of Treating Osteoporitic Fractures in the United Kingdom Female Population" Osteoporosis Int. (1998) vol. 8, pp. 611-617.*
Hassan et al. "Phosphoramidon, an Endotherlin Converting Enzyme Inhibitor Attenuates Local Gastric Ischemia-Reperfusion Injury in Rats" Life Sciences (1997) vol. 61, No. 10, pp. PL 141-147.*
DuBois et al., "Role of abnormal neutral endopeptidase-like activities in HYP mouse bone cells in renal phosphate transport" American Journal of Physiology: Cell Physiology (2002) C1414-C1421.*

Du, L. et al., *cDNA Cloning of the Murine Pex Gene Implicated in X-Linked Hypophosphatemia and Evidence for Expression in Bone*, GENOMICS (1996) vol. 36, Article 0421, pp. 22-28, © Academic Press, Inc.
The HYP Consortium, *A Gene (PEX) With Homologies to endopeptidases is Mutated in Patients With X-Linked Hypophosphatemic Rickets*, Nature Genetics (1995), vol. 11 pp. 130-136, © The American Society for Clinical Investigation Inc.
Beck, Laurent et al., *Pex/PEX Tissue Distribution and Evidence for a Deletion in the 3' Region of the Pex Gene in X-Linked Hypophosphatemic Mice*, Journal of Clinical Investigation, (1997) vol. 99, No. 6, pp. 1200-1209.
Grieff, Marvin et al., *Expression and Cloning of the Human X-Linked Hypophosphatemia Gene cDNA*, Biochemical and Biophysical Research Communications (1997), vol. 231, Article No. RC9976153, pp. 635-639., © Academic Press.
Guo, Rong et al., *Cloning and Sequencing of Human PEX from a Bone cDNA Library: Evidence for Its Developmental Stage-Specific Regulation in Osteoblasts*, Journal of Bone and Mineral Research (1997), vol. 12, No. 7, pp. 1009-1017, © American Society for Bone and Mineral Research.
Lipman, Mark L. et al., *Cloning of Human PEX cDNA: Expression, Subcellular Localization, and Endopeptidase Activity*, The Journal of Biological Chemistry (1998) vol. 273, No. 22, pp. 13729-13737, © The American Society for Biochemistry and Molecular Biology, Inc., Printed in U.S.A.
Schneider, Hans-Gerhard et al., *Parathyroid Hormone-Related Protein mRNA and Protein Expression in Multiple Myeloma : A Case Report*, Journal of Bone and Mineral Research (1998), vol. 13, No. 10, pp. 1640-1643, © American Society for Bone and Mineral Research.
Guise, Theresa A. et al. *Evidence for a Casual Role of Parathyroid Hormone-related Protein in the Pathogenisis of Human Breast Cancer-mediated Osteolysis*, Journal of Clinical Investigation (1996), vol. 98, No. 7, pp. 1544-1549, © The American Society for Clinical Investigation, Inc.
Verma, Inder M. et al., *Gene Therapy—Promises, Problems and Prospects*, Nature (1977), vol. 389, pp. 239-242, © Macmillan Publishers Ltd.

(Continued)

*Primary Examiner*—Shaojia Anna Jiang
*Assistant Examiner*—Eric S Olson
(74) *Attorney, Agent, or Firm*—Trevor Newton; Ogilvy Renault LLP

(57) ABSTRACT

The present invention relates to a method of treating metabolic bone diseases in a patient, which comprises the modulation of PEX activity to modulate the bone micro-environmental concentrations of critical bone anabolic agents, namely PTH and PTHrP. The present invention also provides the use Of inhibitors of PEX activity, such as, the use of inhibitors of NEP and/or ECE and/or PEX such as phosphoramidon, and analogs thereof, to modulate and preferably increase PTH/PTHrP levels in bone microenvironment to consequently result in an increase in bone formation, as confirmed by serum bone markers, namely, osteocalcin, to thereby provide a novel method for treating metabolic bone diseases, such as osteomalacia, osteoporosis, osteopetrosis, Paget's disease and X-linked hypophosphatemic rickets.

3 Claims, 21 Drawing Sheets

OTHER PUBLICATIONS

Anderson, W. French, *Human Gene Therapy*, Nature, vol. 392/Supp, pp. 25-30, © Macmillan Publishers Ltd.

Romano, Gaetano et al., *Latest Developments in Gene Transfer Technology: Achievements, Perspectives, and Controversies over Therapeutic Applications*, Stem Cells 2000, vol. 18, pp. 19-39.

Keibzak, Gary M. et al., *Secondary Hyperparathyroidism in X-Linked Hypophosphatemic Mice*, Endocrinology (1982), vol. 111, No. 2, pp. 650-652, © The Endocrine Society, Published in U.S.A.

Blydt-Hansen, Tom D. et al., *PHEX Expression in Parathyroid Gland and Parathyroid Hormone Dysregulation in X-Linked Hypophosphatemia*, Pediatr. Nephrol. (1999), vol. 13, pp. 607-611. © IPNA.

Econs, Michael et al., *Positional Cloning of the PEX Gene: New Insights Into the Pathophysiology of X-Linked Hypophosphatemic Rickets*, American Journal of Physiology—Renal Physiology (1997) vol. 42, pp. F489-F498.

Zmuda, Joseph M., *Recent Progress in Understanding the Genetic Susceptibility to Osteoporosis*, Genetic Epidemiolgy (1999), vol. 16, pp. 356-367, © Wiley-Liss, Inc.

Friedman, E.A., Consequences and management of hyperphosphatemia in patients with renal insufficiency. Kidney Int Suppl. Jun. 2005;(95):S1-7. Review.

* cited by examiner

```
1
GAT CCA CTA GTA ACG GCC GCC AGT GTG GTG GAA TTC AAG GGA CTC ACA CAC TGA AAG AAT
61                                           31
ATC TTT GAT GAA GAC AAT TCA GGC AAG CAG AAT GAT TCT TGC AAC AGA ATT ACA TGA TTA
121                                          91
ATT GAG ATC TTG AAG TGG GTC CGG TGA ATC CTG GCC ACC TAA CTT ATC ATG ATT TGG GGG
181                                         151
AGT TTC ACG AGA ATC CAG TTT TGA TAA AAC AAT TGT TTT CCT CCC CAA GTG ACT ATA
241                                         211
CAT TTA AAT AGC TAA AAC ATC CCA AAC CTG CCA TAG TAA ACA ACT ATA TAT ACT CGG AAC GCT
301                                         271
TGA GAG AAG AGC CTG TCT AGT CAG GGG GGA CAA AAG CCA AGG GAG CAC CAA ATA TTT TTA TAA
361                                         331
CTG TTT GTT TTG TCT AAG AAT TAT TTG AGA AAG GAC TTT GCT GAG GGA ATT TGG TTT TTA TAA
421                                         391
TTT TCA TTT GTG AAG CTG TCC ATT AGT AGA AGA GCA GAA AAG TGA CCA AGG CAA CCA ATA TTT TGG CGA ATT TCC TGA CGG CAG
481                                         451
TTT CTT AAG CTG CCA CCA AAC CAC GAA ACA GGG AGC AGC GTG AGA GAG CTT TCT TCT CGT AAG AAG CCT TGG ATG TCA CTC TCT ACG GCC CTT
541                                         511
TGA GAC CAG CCA GAA GCA GAA ACT GGA ACT GAG AGC GTG AGC AGC TGA CTT TCT TCT GGA ACT
601 /1                                       571
CTG ATG GAA GCA GAA ACT GGA ACT GAG AGC GTG AGC AGC TGA CTT TCT TCT GGA ACT
    M   E   A   E   T   G   S   S   V   E   T
                                            631/10
CGA ATT GCC CTG GTC GTG TTT GTC GGT GGC ACC CTA GTT CTG GGC ACG ATC CTC TTT CTA
    R   I   A   L   V   V   F   V   G   G   T   L   V   L   G   T   I   L   F   L (cont.)
661/20                                      691/30
```

FIG. 2A (cont.)

721/40
GTG AGT CAA GGT CTC TTA AGT CTC CAA GCT AAA CAG GAG TAC TGC CTG AAG CCA GAA TGC
 V   S   Q   G   L   L   S   L   Q   A   K   Q   E   Y   C   L   K   P   E   C
781/60                                        751/50
ATC GAA GCG GCT GCT GCC ATC TTA AGT AAA TCT GTG GAT CCT TGT GAT ATG CCA
 I   E   A   A   A   A   I   L   S   K   S   V   D   P   C   D   M   P
841/90                                        811/70
TTC TTC CGG TTC GCT TGT GAT GGC ATA AGC AAT AAT CCA ATT CCC GAA GAT ATG CCA
 F   F   R   F   A   C   D   G   I   S   N   N   P   I   P   E   D   M   P
901/100                                       871/90
AGC TAT GGG GTT TAT CCT TGG CTG AGA CAT GTT GAC CTC AAG TTG AAG GAA CTT TTG
 S   Y   G   V   Y   P   W   L   R   H   V   D   L   K   L   K   E   L   L
961/120                                       931/110
GAG AAA TCA ATC AGT AGA CGG GAC ACC ATA CAG AAA GCC AAA CCA CTG GAA ATC CTT TAT
 E   K   S   I   S   R   R   D   T   I   Q   K   A   K   P   L   E   I   L   Y
1021/140                                      991/130
TCA TCC TGC ATG AAT GAG AAA TTC AGC CTT GCA ACG TTT GCA CCA CTA CAC ATC
 S   S   C   M   N   E   K   F   S   L   A   T   F   A   P   L   H   I
1081/160                                      1051/150
CTA CGG CAT TCA CCT TTC CGC TGG CCC GTG CTT CTG CAG GCC AAG CCT GAA GGG GTT
 L   R   H   S   P   F   R   W   P   V   L   L   Q   A   K   P   E   G   V
1141/180                                      1111/170
TGG TCA GAG AGA AAG TTC AGC CTT CTG CAG ACA CTT GCA CTT CGT GGT CAA TAC AGC
 W   S   E   R   K   F   S   L   L   Q   T   L   A   L   R   G   Q   Y   S
1201/200                                      1171/190
AAT TCT GTG TTC ATC CGT TTG TAT GTG TCC CCT GAT GAC AAA GCA TCC AAT GAA CAT ATC
 N   S   V   F   I   R   L   Y   V   S   P   D   D   K   A   S   N   E   H   I
                                              1231/210

FIG-2A (cont.)

```
1261/220                                                                    1291/230
TTG AAG CTG GAC CAA GCA ACA CTC TCC CTG  GCC GTG AGG GAA GAC TAC CTT GAT AAC AGT
 L   K   L   D   Q   A   T   L   S   L   A   V   R   E   D   Y   L   D   N   S
1321/240                                                                    1351/250
ACA GAA GCC AAG TCT TAT CGG GAT GCC CTT  TAC AAG TTC ATG GTG GAT ACT GCC GTG CTT
 T   E   A   K   S   Y   R   D   A   L   Y   K   F   M   V   D   T   A   V   L
1381/260                                                                    1411/270
TTA GGA GCT AAC AGT TCC AGA GCA GAG CAT  GAC ATG AAG TCA GTG CTC AGA TTG GAA ATT
 L   G   A   N   S   S   R   A   E   H   D   M   K   S   V   L   R   L   E   I
1441/280                                                                    1471/290
AAG ATA GCT GAG ATA ATG ATT CCA CAT GAA  AAC CGA ACC AGC GAG GCC ATG TAC AAC AAA
 K   I   A   E   I   M   I   P   H   E   N   R   T   S   E   A   M   Y   N   K
1501/300                                                                    1531/310
ATG AAC ATT TCT GAA CTG AGT GCT ATG ATT  CCC CAG TTC GAC TGG CTG GGC TAC ATC AAG
 M   N   I   S   E   L   S   A   M   I   P   Q   F   D   W   L   G   Y   I   K
1561/320                                                                    1591/330
AAG GTC ATT GAC ACC AGA CTC TAC CCC CAT  CTG AAA GAC ATC AGC CCC TCC GAG AAT GTG
 K   V   I   D   T   R   L   Y   P   H   L   K   D   I   S   P   S   E   N   V
1621/340                                                                    1651/350
GTG GTC CGC GTC CCG CAG TAC TTT AAA GAT  TTG TTT AGG ATA TTA GGG TCT GAG AGA AAG
 V   V   R   V   P   Q   Y   F   K   D   L   F   R   I   L   G   S   E   R   K
1681/360                                                                    1711/370
AAG ACC ATT GCC AAC ATT GTT TAT TTG GTG  ATG GTT TAT TCC AGA ATT CCA AAC CTT AGC
 K   T   I   A   N   I   V   Y   L   V   M   V   Y   S   R   I   P   N   L   S
1741/380                                                                    1771/390
AGG CGC TTT CAG TAT AGA TGG CTG GAA TTC  TCA AGG GTA ATC CAG GGG ACC ACA ACT TTG
 R   R   F   Q   Y   R   W   L   E   F   S   R   V   I   Q   G   T   T   T   L
```

FIG. 2A (cont.)

1801/400
CTG CCT CAA TGG GAC AAA TGT GTA AAC TTT ATT GAA AGT GCC CTC CCT TAT GTT GTT GGA
 L   P   Q   W   D   K   C   V   N   F   I   E   S   A   L   P   Y   V   V   G
1861/420                                         1831/410
AAG ATG TTT GTA GAT GTG TAC TTC CAG GAA GAT AAG AAG GAA ATG GAG ATG GAA TTG GTT
 K   M   F   V   D   V   Y   F   Q   E   D   K   K   E   M   E   M   E   L   V
1921/440                                         1891/430
GAG GGC GTT CGC TGG GCC TTT ATT GAC ATG CTA GAG AAA AAT GAG TGG ATG GAT GCA
 E   G   V   R   W   A   F   I   D   M   L   E   K   N   E   W   M   D   A
1981/460                                         1951/450
GGA ACG AAA AGG AAA GCC AAA GAA AAG GCG AGA GCT GTT TTG GCA AAA GCT ATC CCA
 G   T   K   R   K   A   K   E   K   A   R   A   V   L   A   K   A   I   P
2041/480                                         2011/470
GAG TTT ATA ATG AAT GAT ACT CAT GTT AAT GAA GAC CTC AAA TAT TTA TCA GAA
 E   F   I   M   N   D   T   H   V   N   E   D   L   K   Y   L   S   E
2101/500                                         2071/490
GCC GAC TAC TTT GGC AAC GTC CTA CAA ACT CGC AAG TAT TTA GCA CAG TCT GAT TTC TTC
 A   D   Y   F   G   N   V   L   Q   T   R   K   Y   L   A   Q   S   D   F   F
2161/520                                         2131/510
TGG CTA AGA AAA GCC GTT CCA AAA ACA GAG TGG TTT ACA AAT CCG ACG ACT GTC AAT GCC
 W   L   R   K   A   V   P   K   T   E   W   F   T   N   P   T   T   V   N   A
2221/540                                         2191/530
TTC TAC AGT GCA TCC AAC CAG ATC CGA TTT CCA GCA GGA GAG CTC CAG AAG CCT TTC
 F   Y   S   A   S   N   Q   I   R   F   P   A   G   E   L   Q   K   P   F
2281/560                                         2251/550
TTT TGG GGA ACA GAA TAT CCT CGA TCT CTG AGT GGT TAT GGT GCT ATA GGA GTA ATT GTC GGA
 F   W   G   T   E   Y   P   R   S   L   S   G   Y   G   A   I   G   V   I   V   G
                                                 2311/570

FIG. 2A (cont.)

```
2341/580
CAT GAA TTT ACA CAT GGA TTT GAT AAA AAT GGA AAC CTG
 H   E   F   T   H   G   F   D   K   N   G   N   L
2401/600                                     2371/590
GAT CCT TGG TGG TCT ACT GAA TCA GAA GAA TAT AGA AAA AAT GGT AGA AAA
 D   P   W   W   S   T   E   S   E   E   Y   R   K   N   G   R   K
2461/620                                     2431/610
AAC CAG TAT AGC AAC TAT TGG AAG AAA AAG TTT AAG GAA AAA ACA AAA TGC ATG ATT
 N   Q   Y   S   N   Y   W   K   K   K   F   K   E   K   T   K   C   M   I
2521/640                                     2491/630
CTG GGA GAA AAT ATT GCT GAT AAT GGA CTT GAG AAA GCT GGC TTA AAT GTC AAG GGG AAG AGG ACC
 L   G   E   N   I   A   D   N   G   L   E   K   A   G   L   N   V   K   G   K   R   T
2581/660                                     2551/650
TGG ATA AAT GAC AGA AGG CAG GGA CTC TTC AGT TAT GCT TTT AGG CCA GGC ATC ACA TTC ACC
 W   I   N   D   R   R   Q   G   L   F   S   Y   A   F   R   P   G   I   T   F   T
2641/680                                     2611/670
AAC AAC CAG CTC TTC TTC CTG AGT CAA ATT GGT GCT CAT GTG AGG TGC AAT TCC TAC AGA CCA GAA
 N   N   Q   L   F   F   L   S   Q   I   G   A   H   V   R   C   N   S   Y   R   P   E
2701/700                                     2671/690
GCT GCC CGA GAA CAA GTC CAA ATT GGT GCT CAC AGT CCC CCT CAG TTT AGG GTC AAT GGT
 A   A   R   E   Q   V   Q   I   G   A   H   S   P   P   Q   F   R   V   N   G
2761/720                                     2731/710
GCA ATT AGT AAC ATG GAC TCC CGA TTT GAA GAA TTC CAG AAA GCT TTT AAC TGT CCA CCC AAT N ACG ATG
 A   I   S   N   M   D   S   R   F   E   E   F   Q   K   A   F   N   C   P   P   N   T   M
2821/740                                     2791/730
AAC AGA GGC ATG GAC TCC CGA TCC TGC CGA CTC TGG TAG CTG GGA CGC TGG TTT ATG GCA TCC TGA
 N   R   G   M   D   S   R   S   C   R   L   W   *
2851                                                                    FIG-2A (cont.)
```

```
2881
GAC AGT TGC ACA GTG CCA GCG GAG GCT GCA CTG AGC CTT CAT CGC CCA TTG CTT TAG GCC
2941                                              2971
                                                      2991
TGG AGG AGC TTT CAT TTT TAG TGC ATT TTC ATT ATT TGG GTA GGT GAC CTG CTT GGA TCT
3001                                              3031
AGA CAG CAT CTG TTC AAA GTT GTA GGG CTT ATA AAG TGG AAT ATA AGA AGA ACT AAG TAT
3051                                              3091
GTT TCT TTA GAA AAT CAA ACC AAC AAA AAT AAA TCC CTA GGC TAC TTT TGT TAA AAA AAA
3121
AAA AAA AAA A
```

FIG. 2A (cont.)

```
hPEX                                                             
                 10          20         30         40         50         60
        EAETGSSVETGKKANRGTRIALVVFVGGTLVLGTILFLVSQGLLSLQAKQEYCLKPECIE
         :: :   :   ::    :     ::: :: :: :: .  :::
hNEP    ESQMDITDINTPKPKKKQRWTPLEISLSVLVLLLTIIAVTMIALYATYDDGICKSSDCIK
                 10         20         30         40         50         60 hPEX    AAAAILSKVNLSVDPCDNFFRFACDGWISNNPIPEDMPSYGVYPWLRHNVDLKLKELLEK
                 70         80         90        100        110        120
         :   ::.   :    .:: :: .::    .:::  ::.:  .: ::
hNEP    SAARLIQNMDATTEPCTDFFKYACGGWLKRNVIPETSSRYGNFDILRDELEVVLKDVLQE
                 70         80         90        100        110        120 hPEX    SISRRRDTEAIQKAKILYSSCMNEKAIEKADAKPLLHILRHSPFRWPVLESNIGPEGVWS
                130        140        150        160        170        180
         . :    ::.    :::    :::  :::    :: :  ::   .
hNEP    PKT--EDIVAVQKAKALYRSCINESAIDSRGGEPLLKLLPDI-YGWPVATENWEQKYGAS
                130         140       150        160       170        180 hPEX    ERKFSLLQTLATFRGQYSNSVFIRLYVSPDDKASNEHILKLDQATLSLAVREDYLDNSTE
                190        200        210        220        230        240
          :. ::   :::::.:  ::::::  ::.:::::  :  ::    ::::::  ::
hNEP    W---TAEKAIAQLNSKYGKKVLINLFVGTDDKNSVNHVIHIDQPRLGLPSRDYYECTGIY
                190        200        210        220        230
```

FIG. 2B (cont.)

```
               250         260         270         280         290
                 .    :    .    :    .    :    .    :    .    :
hPEX     AKSYRDALY-KFMVDTAVLLGANSSRAEH----DMKSVLRLEIKIAEIMIPHENRT-SEA
             ::::::  :::::::   .: :::       ::::::::::::::::::::  :::
hNEP     KEACTAYVDFMISVARLIRQEERLPIDENQLALEMNKVMELEKEIANATAKPEDRNDPML
               240         250         260         270         280         290

300         310         320         330         340         350
                 .    :    .    :    .    :    .    :    .    :    .    :
hPEX     MYNKMNISEL-SAMIPQFDWLGYIK-KVIDTRLYPHLKDISPSENVVVRVPQYFKDLFRI
         ::::::::::  :::::::::::::  ::::::::::::::::::::: :::::::::::
hNEP     LYNKMTLAQIQNNFSLEINGKPFSWLNFTNEIMSTVNISITNEEDVVVYAPEYLTKLKPI
               300         310         320         330         340         350

360         370         380         390         400         410
                 .    :    .  ::    .    :    .    :    .    :    .    :
hPEX     LGSERKKTIANYLVWRMVYSRIPNLSRRFQYRWLEFSRVIQGTTTLLPQWDKCVNFIESA
         :::::::::::::::: :::::::::::::::::::: ::: :::::: ::::::::::
hNEP     LTKYSARDLQNLMSWRFIMDLVSSLSRTYKESRNAFRKALYGTTSETATWRRCANYVNGN
               360         370         380         390         400         410
```

FIG. 2B (cont.)

```
hPEX            420        430        440        450        460        470
        LPYVVGKMFVDVYFQEDKKEMMEELVEGVRWAFIDMLEKENEWMDAGTKRKAKEKARAVL
                :::::::: .  : :::::::::::::::::::::::::::::::::::
hNEP    MENAVGRLYVEAAFAGESKHVVEDLIAQIREVFIQTLD-DLTWMDAETKKRAEEKALAIK
                420        430        440        450        460        470 hPEX            480        490        500        510        520        530
        AKVGYPEFIM-NDTHVNEDLKAIKFSEADYFGNVLQTRKYLAQSDFFWLRKAVPKTEWFT
         :::::: ::  :: : ::::::::::::::::::::::::::::::::::::::
hNEP    ERIGYPDDIVSNDNKLNNEYLELNYKEDEYFENIIQNLKFSQSKQLKKLREKVDKDEWIS
                480        490        500        510        520        530 hPEX            540        550        560        570        580        590
        NPTTVNAFYSASTNQIRFPAGELQKPFFWGTEYPRSLSYGAIGVIVGHEFTHGFDNNGRK
         ::: ::::::: ::::::::: :::: ::: :::::::::::::::::::::::::::
hNEP    GAAVVNAFYSSGRNQIVFPAGILQPPFFSAQQSN-SLNYGGIGMVIGHEITHGFDDNGRN
                540        550        560        570        580        590
```

FIG. 2B (cont.)

```
              600        610        620        630        640        650
hPEX   YDKNGNLDPWWSTESEEKFKEKTKCMINQYSNYYWKKAG-LNVVKGKRTLGENIADNGGLR
            : ::: .: ::    : ::   .:     .  ::  :::.:::::::::
hNEP   FNKDGDLVDWWTQQSASNFKEQSQCMVYQYGNFSWDLAGGQHLNGINTLGENIADNGGLG
              600        610        620        630        640        650

660        670        680        690        700        710
hPEX   EAFRAYRKWINDRRQGLEEPLLPGITFTNNQLFFLSYAHVRCNSYRPEAAREQVQIGAHS
        :  :::: ::::::   ::    ::   :: :::.:::::  ::::  ::
hNEP   QAYRAYQ---NYIKNGEEKLLPGLDLNHKQLFFLNFAQVWCGTYRPEYAVNSIKTDVHS
              660        670        680        690        700        710

720        730        740        750
hPEX   PPQFRVNGAISNFEEFQKAFNCPPNSTMNRGMDSCRLW
        : :: :  :::::::  ::  ::.: :::  ::: :
hNEP   PGNFRIIGTLQNSAEFSEAFHCRKNSYMNPEKK-CRVW
              720        730        740        750
```

FIG.—2B (cont.)

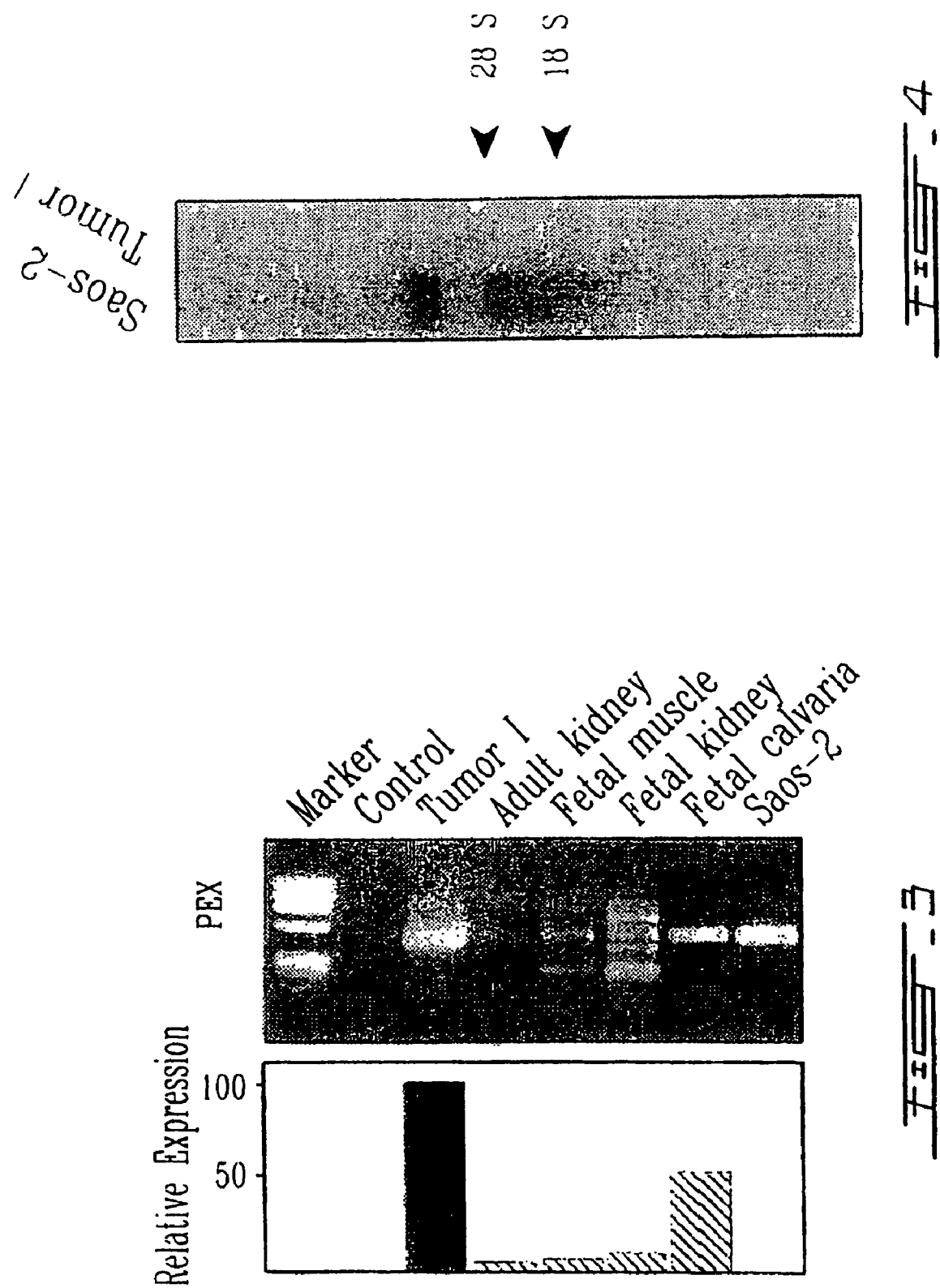

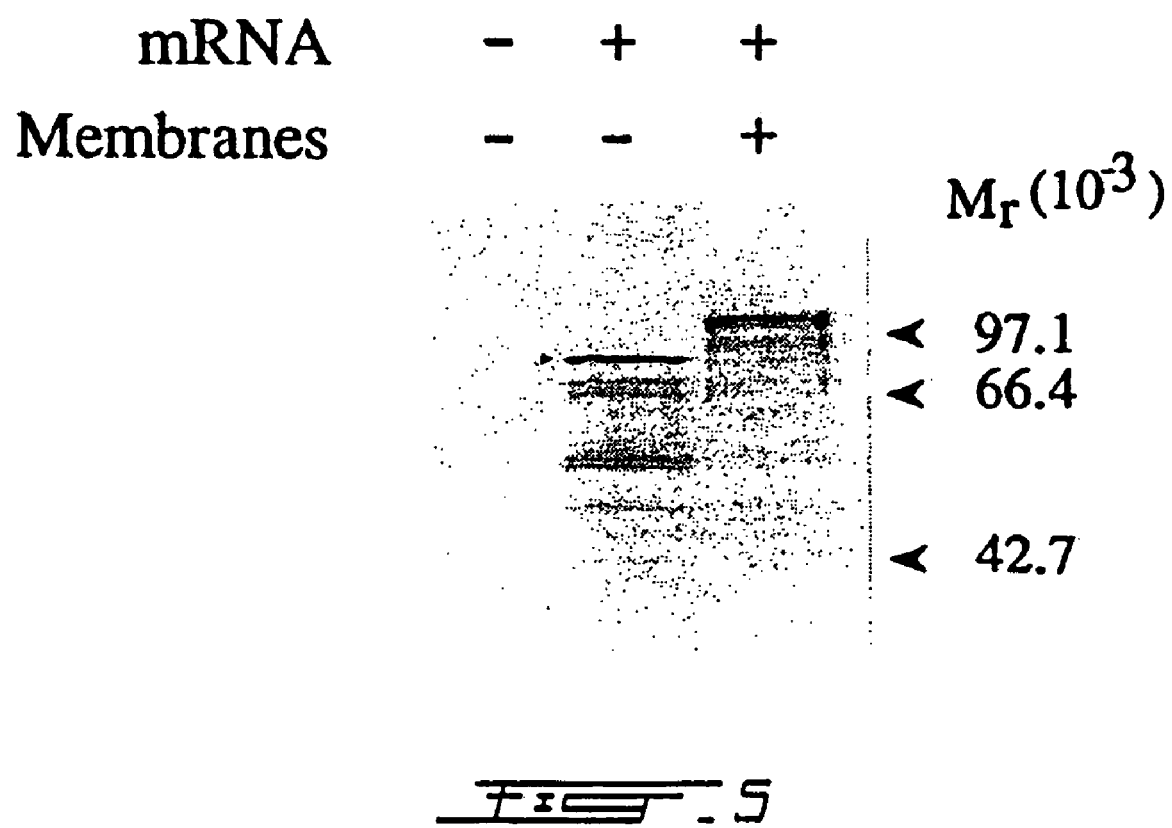

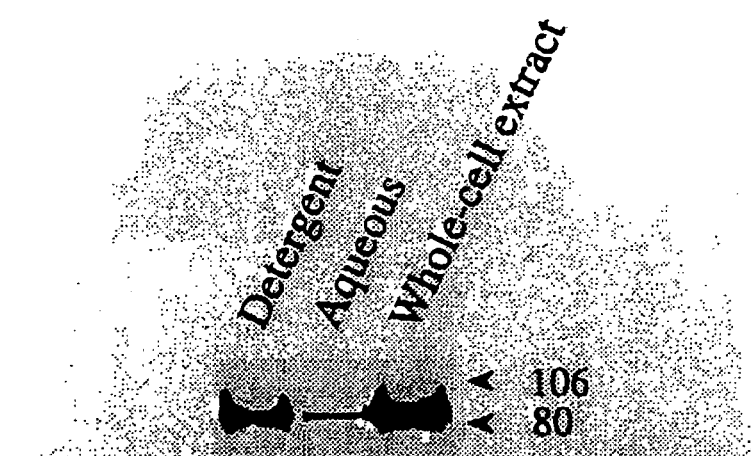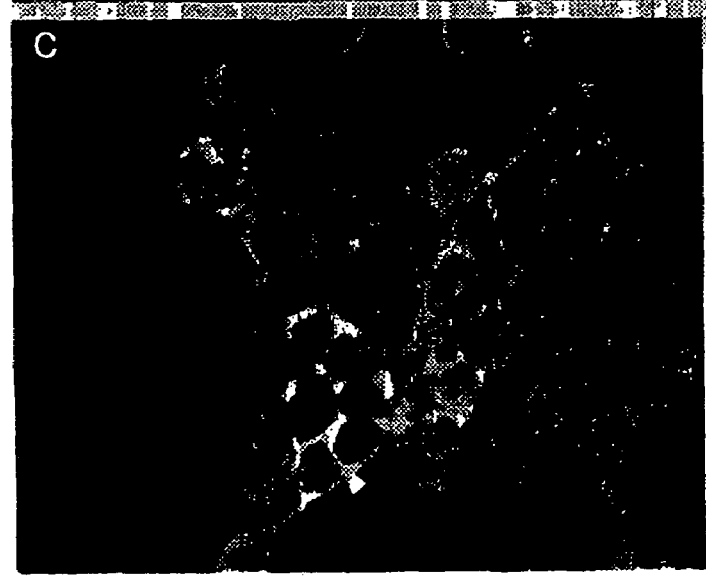
FIG. 6

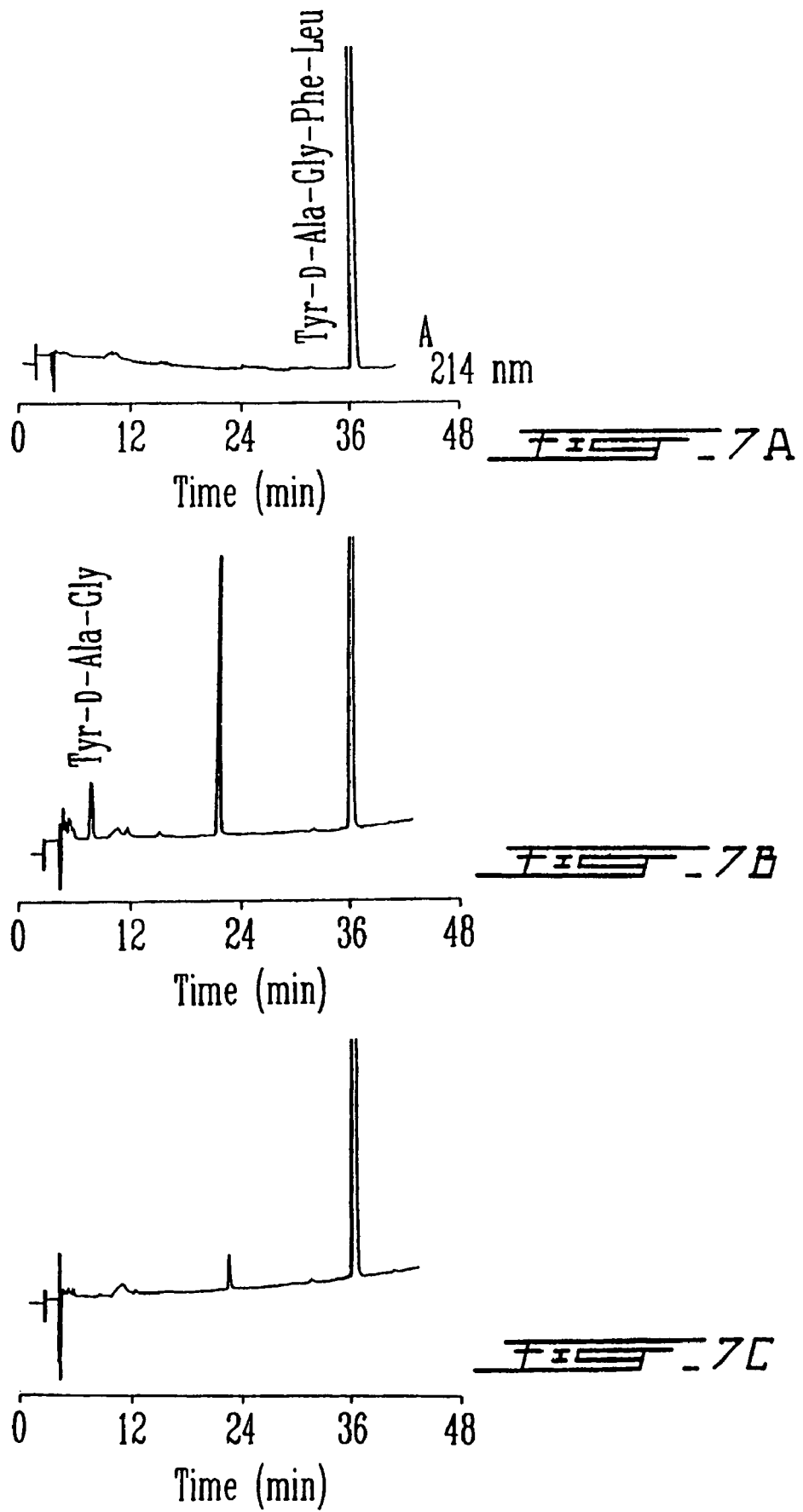

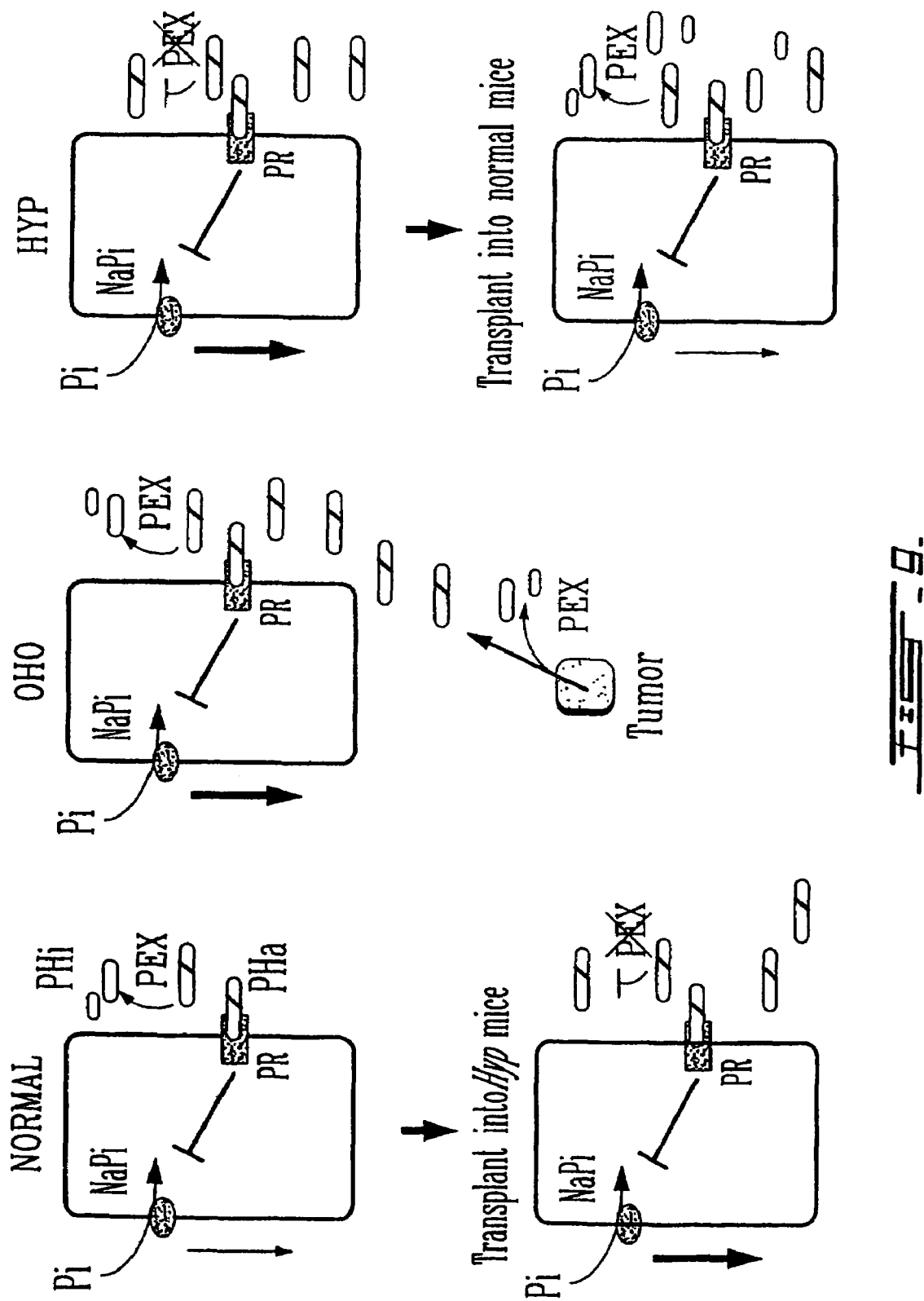

SEQUENCE LISTING

```
<160> NUMBER OF SEQ ID NOS: 11

<210> SEQ ID NO 1
<211> LENGTH: 3130
<212> TYPE: DNA
<213> ORGANISM: Human PEX
<220> FEATURE:
<221> NAME/KEY: CDS
<222> LOCATION: (604)...(2848)

<400> SEQUENCE: 1
gatccactag taacggccgc cagtgtggtg gaattcaagg gactcacaca ctgaaagaat      60
atctttgatg aagacaattc aggcaagcag aatgattctt gcaacagaat tacatgatta     120
attgagatct tgaagtgggt ccggtgaatc ctggccacct aacttatcat gatttggggg     180
agtttcacga gaatccagtt ttgataaaac aattgttttt ttcctcccca agtgactata     240
catttaaata gctaaaacat ctgttcagca acatagtaaa acatatatac tcggaacgct     300
tgagagaaga gcctgccaaa cagggacttt gctgagggag agcaccaaga taaagcaaca     360
ctgtttgttt tgtctagtca gggggggaaag ccaaggcaac caatattttg gtttttataa    420
ttttcatttg tgaagaatta tttgagaaag ggttggcgag gggagatttc ctgacggcag     480
tttcttaagc tgtccattag tagaagagca agagagcctt ggatgtcaac gcctcgctct     540
tgagaccagc caccaaacca cgaaaagtga ctttcttctc gtgtgctctc tacggccctt     600 ctg atg gaa gca gaa aca ggg agc agc gtg gag act gga aag aag gcc      648
    Met Glu Ala Glu Thr Gly Ser Ser Val Glu Thr Gly Lys Lys Ala
    1               5                  10                   15 aac aga ggc act cga att gcc ctg gtc gtg ttt gtc ggt ggc acc cta      696
Asn Arg Gly Thr Arg Ile Ala Leu Val Val Phe Val Gly Gly Thr Leu
                 20                  25                  30 gtt ctg ggc acg atc ctc ttt cta gtg agt caa ggt ctc tta agt ctc      744
Val Leu Gly Thr Ile Leu Phe Leu Val Ser Gln Gly Leu Leu Ser Leu
             35                  40                  45 caa gct aaa cag gag tac tgc ctg aag cca gaa tgc atc gaa gcg gct      792
Gln Ala Lys Gln Glu Tyr Cys Leu Lys Pro Glu Cys Ile Glu Ala Ala
         50                  55                  60 gct gcc atc tta agt aaa gta aat ctg tct gtg gat cct tgt gat aat      840
Ala Ala Ile Leu Ser Lys Val Asn Leu Ser Val Asp Pro Cys Asp Asn
     65                  70                  75 ttc ttc cgg ttc gct tgt gat ggc tgg ata agc aat aat cca att ccc      888
Phe Phe Arg Phe Ala Cys Asp Gly Trp Ile Ser Asn Asn Pro Ile Pro
 80                  85                  90                  95
```

```
gaa gat atg cca agc tat ggg gtt tat cct tgg ctg aga cat aat gtt      936
Glu Asp Met Pro Ser Tyr Gly Val Tyr Pro Trp Leu Arg His Asn Val
            100                 105                 110 gac ctc aag ttg aag gaa ctt ttg gag aaa tca atc agt aga agg cgg      984
Asp Leu Lys Leu Lys Glu Leu Leu Glu Lys Ser Ile Ser Arg Arg Arg
        115                 120                 125 gac acc gaa gcc ata cag aaa gcc aaa atc ctt tat tca tcc tgc atg     1032
Asp Thr Glu Ala Ile Gln Lys Ala Lys Ile Leu Tyr Ser Ser Cys Met
    130                 135                 140 aat gag aaa gcg att gaa aaa gca gat ggc aag cca ctg cta cac atc     1080
Asn Glu Lys Ala Ile Glu Lys Ala Asp Gly Lys Pro Leu Leu His Ile
145                 150                 155 cta cgg cat tca cct ttc cgc tgg ccc gtg ctt gaa tct aat att ggc     1128
Leu Arg His Ser Pro Phe Arg Trp Pro Val Leu Glu Ser Asn Ile Gly
160                 165                 170                 175 cct gaa ggg gtt tgg tca gag aga aag ttc agc ctt ctg cag aca ctt     1176
Pro Glu Gly Val Trp Ser Glu Arg Lys Phe Ser Leu Leu Gln Thr Leu
            180                 185                 190 gca acg ttt cgt ggt caa tac agc aat tct gtg ttc atc cgt ttg tat     1224
Ala Thr Phe Arg Gly Gln Tyr Ser Asn Ser Val Phe Ile Arg Leu Tyr
        195                 200                 205 gtg tcc cct gat gac aaa gca tcc aat gaa cat atc ttg aag ctg gac     1272
Val Ser Pro Asp Asp Lys Ala Ser Asn Glu His Ile Leu Lys Leu Asp
    210                 215                 220 caa gca aca ctc tcc ctg gcc gtg agg gaa gac tac ctt gat aac agt     1320
Gln Ala Thr Leu Ser Leu Ala Val Arg Glu Asp Tyr Leu Asp Asn Ser
225                 230                 235 aca gaa gcc aag tct tat cgg gat gcc ctt tac aag ttc atg gtg gat     1368
Thr Glu Ala Lys Ser Tyr Arg Asp Ala Leu Tyr Lys Phe Met Val Asp
240                 245                 250                 255 act gcc gtg ctt tta gga gct aac agt tcc aga gca gag cat gac atg     1416
Thr Ala Val Leu Leu Gly Ala Asn Ser Ser Arg Ala Glu His Asp Met
            260                 265                 270 aag tca gtg ctc aga ttg gaa att aag ata gct gag ata atg att cca     1464
Lys Ser Val Leu Arg Leu Glu Ile Lys Ile Ala Glu Ile Met Ile Pro
        275                 280                 285 cat gaa aac cga acc agc gag gcc atg tac aac aaa atg aac att tct     1512
His Glu Asn Arg Thr Ser Glu Ala Met Tyr Asn Lys Met Asn Ile Ser
    290                 295                 300 gaa ctg agt gct atg att ccc cag ttc gac tgg ctg ggc tac atc aag     1560
Glu Leu Ser Ala Met Ile Pro Gln Phe Asp Trp Leu Gly Tyr Ile Lys
305                 310                 315 aag gtc att gac acc aga ctc tac ccc cat ctg aaa gac atc agc ccc     1608
Lys Val Ile Asp Thr Arg Leu Tyr Pro His Leu Lys Asp Ile Ser Pro
320                 325                 330                 335 tcc gag aat gtg gtg gtc cgc gtc ccg cag tac ttt aaa gat ttg ttt     1656
Ser Glu Asn Val Val Val Arg Val Pro Gln Tyr Phe Lys Asp Leu Phe
            340                 345                 350 agg ata tta ggg tct gag aga aag aag acc att gac aac tat ttg gtg     1704
Arg Ile Leu Gly Ser Glu Arg Lys Lys Thr Ile Asp Asn Tyr Leu Val
        355                 360                 365 tgg aga atg gtt tat tcc aga att cca aac ctt agc agg cgc ttt cag     1752
Trp Arg Met Val Tyr Ser Arg Ile Pro Asn Leu Ser Arg Arg Phe Gln
    370                 375                 380 tat aga tgg ctg gaa ttc tca agg gta atc cag ggg acc aca act ttg     1800
Tyr Arg Trp Leu Glu Phe Ser Arg Val Ile Gln Gly Thr Thr Thr Leu
385                 390                 395 ctg cct caa agg gac aaa tgt gta aac ttt att gaa agt gcc ctc cct     1848
Leu Pro Gln Arg Asp Lys Cys Val Asn Phe Ile Glu Ser Ala Leu Pro
400                 405                 410                 415
```

```
tat gtt gtt gga aag atg ttt gta gat gtg tac ttc cag gaa gat aag     1896
Tyr Val Val Gly Lys Met Phe Val Asp Val Tyr Phe Gln Glu Asp Lys
                420                 425                 430 aag gaa atg atg gag gaa ttg gtt gag ggc gtt cgc tgg gcc ttt att     1944
Lys Glu Met Met Glu Glu Leu Val Glu Gly Val Arg Trp Ala Phe Ile
            435                 440                 445 gac atg cta gag aaa gaa aat gag tgg atg gat gca gga acg aaa agg     1992
Asp Met Leu Glu Lys Glu Asn Glu Trp Met Asp Ala Gly Thr Lys Arg
        450                 455                 460 aaa gcc aaa gaa aag gcg aga gct gtt ttg gca aaa gtt ggc tat cca     2040
Lys Ala Lys Glu Lys Ala Arg Ala Val Leu Ala Lys Val Gly Tyr Pro
    465                 470                 475 gag ttt ata atg aat gat act cat gtt aat gaa gac ctc aaa gct atc     2088
Glu Phe Ile Met Asn Asp Thr His Val Asn Glu Asp Leu Lys Ala Ile
480                 485                 490                 495 aag ttt tca gaa gcc gac tac ttt ggc aac gtc cta caa act cgc aag     2136
Lys Phe Ser Glu Ala Asp Tyr Phe Gly Asn Val Leu Gln Thr Arg Lys
                500                 505                 510 tat tta gca cag tct gat ttc ttc tgg cta aga aaa gcc gtt cca aaa     2184
Tyr Leu Ala Gln Ser Asp Phe Phe Trp Leu Arg Lys Ala Val Pro Lys
            515                 520                 525 aca gag tgg ttt aca aat ccg acg act gtc aat gcc ttc tac agt gca     2232
Thr Glu Trp Phe Thr Asn Pro Thr Thr Val Asn Ala Phe Tyr Ser Ala
        530                 535                 540 tcc acc aac cag atc cga ttt cca gca gga gag ctc cag aag cct ttc     2280
Ser Thr Asn Gln Ile Arg Phe Pro Ala Gly Glu Leu Gln Lys Pro Phe
    545                 550                 555 ttt tgg gga aca gaa tat cct cga tct ctg agt tat ggt gct ata gga     2328
Phe Trp Gly Thr Glu Tyr Pro Arg Ser Leu Ser Tyr Gly Ala Ile Gly
560                 565                 570                 575 gta att gtc gga cat gaa ttt aca cat gga ttt gat aat aat ggt aga     2376
Val Ile Val Gly His Glu Phe Thr His Gly Phe Asp Asn Asn Gly Arg
                580                 585                 590 aaa tat gat aaa aat gga aac ctg gat cct tgg tgg tct act gaa tca     2424
Lys Tyr Asp Lys Asn Gly Asn Leu Asp Pro Trp Trp Ser Thr Glu Ser
            595                 600                 605 gaa gaa aag ttt aag gaa aaa aca aaa tgc atg att aac cag tat agc     2472
Glu Glu Lys Phe Lys Glu Lys Thr Lys Cys Met Ile Asn Gln Tyr Ser
        610                 615                 620 aac tat tat tgg aag aaa gct ggc tta aat gtc aag ggg aag agg acc     2520
Asn Tyr Tyr Trp Lys Lys Ala Gly Leu Asn Val Lys Gly Lys Arg Thr
    625                 630                 635 ctg gga gaa aat att gct gat aat gga ggc ctg cgg gaa gct ttt agg     2568
Leu Gly Glu Asn Ile Ala Asp Asn Gly Gly Leu Arg Glu Ala Phe Arg
640                 645                 650                 655 gct tac agg aaa tgg ata aat gac aga agg cag gga ctt gag gag cct     2616
Ala Tyr Arg Lys Trp Ile Asn Asp Arg Arg Gln Gly Leu Glu Glu Pro
                660                 665                 670 ctt cta cca ggc atc aca ttc acc aac aac cag ctc ttc ttc ctg agt     2664
Leu Leu Pro Gly Ile Thr Phe Thr Asn Asn Gln Leu Phe Phe Leu Ser
            675                 680                 685 tat gct cat gtg agg tgc aat tcc tac aga cca gaa gct gcc cga gaa     2712
Tyr Ala His Val Arg Cys Asn Ser Tyr Arg Pro Glu Ala Ala Arg Glu
        690                 695                 700 caa gtc caa att ggt gct cac agt ccc cct cag ttt agg gtc aat ggt     2760
Gln Val Gln Ile Gly Ala His Ser Pro Pro Gln Phe Arg Val Asn Gly
    705                 710                 715 gca att agt aac ttt gaa gaa ttc cag aaa gct ttt aac tgt cca ccc     2808
Ala Ile Ser Asn Phe Glu Glu Phe Gln Lys Ala Phe Asn Cys Pro Pro
```

-continued

```
               720           725           730           735
aat tcc acg atg aac aga ggc atg gac tcc tgc cga ctc t ggtagctggg    2858
Asn Ser Thr Met Asn Arg Gly Met Asp Ser Cys Arg Leu
                740                   745 acgctggttt atgcatcct gagacagttg cacagtgcca gcggaggctg cactgagcct    2918
tcatcgccca ttgctttagg cctggaggag ctttcatttt tagtgcattt tcattatttg    2978
ggtaggtgac ctgcttggat ctagacagca tctgttcaaa gttgtagggc ttataaagtg    3038
gaatataaga agaactaagt atgtttcttt agaaaatcaa accaacaaaa ataaatccct    3098
aggctacttt tgttaaaaaa aaaaaaaaaa aa                                  3130

<210> SEQ ID NO 2
<211> LENGTH: 749
<212> TYPE: PRT
<213> ORGANISM: Human PEX

<400> SEQUENCE: 2

Met Glu Ala Glu Thr Gly Ser Ser Val Glu Thr Gly Lys Lys Ala Asn
 1               5                   10                  15

Arg Gly Thr Arg Ile Ala Leu Val Val Phe Val Gly Gly Thr Leu Val
            20                  25                  30

Leu Gly Thr Ile Leu Phe Leu Val Ser Gln Gly Leu Leu Ser Leu Gln
        35                  40                  45

Ala Lys Gln Glu Tyr Cys Leu Lys Pro Glu Cys Ile Glu Ala Ala Ala
    50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
            100                 105                 110

Leu Lys Leu Lys Glu Leu Leu Glu Lys Ser Ile Ser Arg Arg Arg Asp
        115                 120                 125

Thr Glu Ala Ile Gln Lys Ala Lys Ile Leu Tyr Ser Ser Cys Met Asn
    130                 135                 140

Glu Lys Ala Ile Glu Lys Ala Asp Gly Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
            180                 185                 190

Thr Phe Arg Gly Gln Tyr Ser Asn Ser Val Phe Ile Arg Leu Tyr Val
        195                 200                 205

Ser Pro Asp Asp Lys Ala Ser Asn Glu His Ile Leu Lys Leu Asp Gln
    210                 215                 220

Ala Thr Leu Ser Leu Ala Val Arg Glu Asp Tyr Leu Asp Asn Ser Thr
225                 230                 235                 240

Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
            260                 265                 270

Ser Val Leu Arg Leu Glu Ile Lys Ile Ala Glu Ile Met Ile Pro His
        275                 280                 285

Glu Asn Arg Thr Ser Glu Ala Met Tyr Asn Lys Met Asn Ile Ser Glu
```

```
                290                 295                 300
Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Arg Val Pro Gln Tyr Phe Lys Asp Leu Phe Arg
                340                 345                 350

Ile Leu Gly Ser Glu Arg Lys Lys Thr Ile Asp Asn Tyr Leu Val Trp
                355                 360                 365

Arg Met Val Tyr Ser Arg Ile Pro Asn Leu Ser Arg Arg Phe Gln Tyr
370                 375                 380

Arg Trp Leu Glu Phe Ser Arg Val Ile Gln Gly Thr Thr Thr Leu Leu
385                 390                 395                 400

Pro Gln Arg Asp Lys Cys Val Asn Phe Ile Glu Ser Ala Leu Pro Tyr
                405                 410                 415

Val Val Gly Lys Met Phe Val Asp Val Tyr Phe Gln Glu Asp Lys Lys
                420                 425                 430

Glu Met Met Glu Glu Leu Val Glu Gly Val Arg Trp Ala Phe Ile Asp
                435                 440                 445

Met Leu Glu Lys Glu Asn Glu Trp Met Asp Ala Gly Thr Lys Arg Lys
450                 455                 460

Ala Lys Glu Lys Ala Arg Ala Val Leu Ala Lys Val Gly Tyr Pro Glu
465                 470                 475                 480

Phe Ile Met Asn Asp Thr His Val Asn Glu Asp Leu Lys Ala Ile Lys
                485                 490                 495

Phe Ser Glu Ala Asp Tyr Phe Gly Asn Val Leu Gln Thr Arg Lys Tyr
                500                 505                 510

Leu Ala Gln Ser Asp Phe Phe Trp Leu Arg Lys Ala Val Pro Lys Thr
                515                 520                 525

Glu Trp Phe Thr Asn Pro Thr Thr Val Asn Ala Phe Tyr Ser Ala Ser
                530                 535                 540

Thr Asn Gln Ile Arg Phe Pro Ala Gly Glu Leu Gln Lys Pro Phe Phe
545                 550                 555                 560

Trp Gly Thr Glu Tyr Pro Arg Ser Leu Ser Tyr Gly Ala Ile Gly Val
                565                 570                 575

Ile Val Gly His Glu Phe Thr His Gly Phe Asp Asn Asn Gly Arg Lys
                580                 585                 590

Tyr Asp Lys Asn Gly Asn Leu Asp Pro Trp Trp Ser Thr Glu Ser Glu
                595                 600                 605

Glu Lys Phe Lys Glu Lys Thr Lys Cys Met Ile Asn Gln Tyr Ser Asn
610                 615                 620

Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
                645                 650                 655

Tyr Arg Lys Trp Ile Asn Asp Arg Arg Gln Gly Leu Glu Glu Pro Leu
                660                 665                 670

Leu Pro Gly Ile Thr Phe Thr Asn Asn Gln Leu Phe Phe Leu Ser Tyr
                675                 680                 685

Ala His Val Arg Cys Asn Ser Tyr Arg Pro Glu Ala Ala Arg Glu Gln
                690                 695                 700

Val Gln Ile Gly Ala His Ser Pro Pro Gln Phe Arg Val Asn Gly Ala
705                 710                 715                 720
```

-continued

```
Ile Ser Asn Phe Glu Glu Phe Gln Lys Ala Phe Asn Cys Pro Pro Asn
            725                 730                 735

Ser Thr Met Asn Arg Gly Met Asp Ser Cys Arg Leu Trp
            740                 745

<210> SEQ ID NO 3
<211> LENGTH: 749
<212> TYPE: PRT
<213> ORGANISM: Human PEX

<400> SEQUENCE: 3

Met Glu Ala Glu Thr Gly Ser Ser Val Glu Thr Gly Lys Lys Ala Asn
  1               5                  10                  15

Arg Gly Thr Arg Ile Ala Leu Val Val Phe Val Gly Gly Thr Leu Val
             20                  25                  30

Leu Gly Thr Ile Leu Phe Leu Val Ser Gln Gly Leu Leu Ser Leu Gln
             35                  40                  45

Ala Lys Gln Glu Tyr Cys Leu Lys Pro Glu Cys Ile Glu Ala Ala Ala
         50                  55                  60

Ala Ile Leu Ser Lys Val Asn Leu Ser Val Asp Pro Cys Asp Asn Phe
 65                  70                  75                  80

Phe Arg Phe Ala Cys Asp Gly Trp Ile Ser Asn Asn Pro Ile Pro Glu
                 85                  90                  95

Asp Met Pro Ser Tyr Gly Val Tyr Pro Trp Leu Arg His Asn Val Asp
            100                 105                 110

Leu Lys Leu Lys Glu Leu Leu Glu Lys Ser Ile Ser Arg Arg Arg Asp
        115                 120                 125

Thr Glu Ala Ile Gln Lys Ala Lys Ile Leu Tyr Ser Ser Cys Met Asn
    130                 135                 140

Glu Lys Ala Ile Glu Lys Ala Asp Ala Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
            180                 185                 190

Thr Phe Arg Gly Gln Tyr Ser Asn Ser Val Phe Ile Arg Leu Tyr Val
        195                 200                 205

Ser Pro Asp Asp Lys Ala Ser Asn Glu His Ile Leu Lys Leu Asp Gln
    210                 215                 220

Ala Thr Leu Ser Leu Ala Val Arg Glu Asp Tyr Leu Asp Asn Ser Thr
225                 230                 235                 240

Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
            260                 265                 270

Ser Val Leu Arg Leu Glu Ile Lys Ile Ala Glu Ile Met Ile Pro His
        275                 280                 285

Glu Asn Arg Thr Ser Glu Ala Met Tyr Asn Lys Met Asn Ile Ser Glu
    290                 295                 300

Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Val Arg Val Pro Gln Tyr Phe Lys Asp Leu Phe Arg
```

-continued

```
                340                 345                 350
Ile Leu Gly Ser Glu Arg Lys Lys Thr Ile Ala Asn Tyr Leu Val Trp
            355                 360                 365
Arg Met Val Tyr Ser Arg Ile Pro Asn Leu Ser Arg Arg Phe Gln Tyr
        370                 375                 380
Arg Trp Leu Glu Phe Ser Arg Val Ile Gln Gly Thr Thr Thr Leu Leu
385                 390                 395                 400
Pro Gln Trp Asp Lys Cys Val Asn Phe Ile Glu Ser Ala Leu Pro Tyr
                405                 410                 415
Val Val Gly Lys Met Phe Val Asp Val Tyr Phe Gln Glu Asp Lys Lys
            420                 425                 430
Glu Met Met Glu Glu Leu Val Glu Gly Val Arg Trp Ala Phe Ile Asp
        435                 440                 445
Met Leu Glu Lys Glu Asn Glu Trp Met Asp Ala Gly Thr Lys Arg Lys
    450                 455                 460
Ala Lys Glu Lys Ala Arg Ala Val Leu Ala Lys Val Gly Tyr Pro Glu
465                 470                 475                 480
Phe Ile Met Asn Asp Thr His Val Asn Glu Asp Leu Lys Ala Ile Lys
                485                 490                 495
Phe Ser Glu Ala Asp Tyr Phe Gly Asn Val Leu Gln Thr Arg Lys Tyr
            500                 505                 510
Leu Ala Gln Ser Asp Phe Phe Trp Leu Arg Lys Ala Val Pro Lys Thr
        515                 520                 525
Glu Trp Phe Thr Asn Pro Thr Thr Val Asn Ala Phe Tyr Ser Ala Ser
    530                 535                 540
Thr Asn Gln Ile Arg Phe Pro Ala Gly Glu Leu Gln Lys Pro Phe Phe
545                 550                 555                 560
Trp Gly Thr Glu Tyr Pro Arg Ser Leu Ser Tyr Gly Ala Ile Gly Val
                565                 570                 575
Ile Val Gly His Glu Phe Thr His Gly Phe Asp Asn Asn Gly Arg Lys
            580                 585                 590
Tyr Asp Lys Asn Gly Asn Leu Asp Pro Trp Trp Ser Thr Glu Ser Glu
        595                 600                 605
Glu Lys Phe Lys Glu Lys Thr Lys Cys Met Ile Asn Gln Tyr Ser Asn
    610                 615                 620
Tyr Tyr Trp Lys Lys Ala Gly Leu Asn Val Lys Gly Lys Arg Thr Leu
625                 630                 635                 640
Gly Glu Asn Ile Ala Asp Asn Gly Gly Leu Arg Glu Ala Phe Arg Ala
                645                 650                 655
Tyr Arg Lys Trp Ile Asn Asp Arg Arg Gln Gly Leu Glu Glu Pro Leu
            660                 665                 670
Leu Pro Gly Ile Thr Phe Thr Asn Asn Gln Leu Phe Phe Leu Ser Tyr
        675                 680                 685
Ala His Val Arg Cys Asn Ser Tyr Arg Pro Glu Ala Ala Arg Glu Gln
    690                 695                 700
Val Gln Ile Gly Ala His Ser Pro Pro Gln Phe Arg Val Asn Gly Ala
705                 710                 715                 720
Ile Ser Asn Phe Glu Glu Phe Gln Lys Ala Phe Asn Cys Pro Pro Asn
                725                 730                 735
Ser Thr Met Asn Arg Gly Met Asp Ser Cys Arg Leu Trp
            740                 745
```

<210> SEQ ID NO 4

<211> LENGTH: 747
<212> TYPE: PRT
<213> ORGANISM: Human NEP

<400> SEQUENCE: 4

```
Met Glu Ser Gln Met Asp Ile Thr Asp Ile Asn Thr Pro Lys Pro Lys
 1               5                  10                  15

Lys Lys Gln Arg Trp Thr Pro Leu Glu Ile Ser Leu Ser Val Leu Val
            20                  25                  30

Leu Leu Leu Thr Ile Ile Ala Val Thr Met Ile Ala Leu Tyr Ala Thr
        35                  40                  45

Tyr Asp Asp Gly Ile Cys Lys Ser Ser Asp Cys Ile Lys Ser Ala Ala
 50                  55                  60

Arg Leu Ile Gln Asn Met Asp Ala Thr Thr Glu Pro Cys Thr Asp Phe
 65                  70                  75                  80

Phe Lys Tyr Ala Cys Gly Gly Trp Leu Lys Arg Asn Val Ile Pro Glu
                85                  90                  95

Thr Ser Ser Arg Tyr Gly Asn Phe Asp Ile Leu Arg Asp Glu Leu Glu
            100                 105                 110

Val Val Leu Lys Asp Val Leu Gln Glu Pro Lys Thr Glu Asp Ile Val
        115                 120                 125

Ala Val Gln Lys Ala Lys Ala Leu Tyr Arg Ser Cys Ile Asn Glu Ser
    130                 135                 140

Ala Ile Asp Ser Arg Gly Gly Glu Pro Leu Leu Lys Leu Leu Pro Asp
145                 150                 155                 160

Ile Tyr Gly Trp Pro Val Ala Thr Glu Asn Trp Glu Gln Lys Tyr Gly
                165                 170                 175

Ala Ser Trp Thr Ala Glu Lys Ala Ile Ala Gln Leu Asn Ser Lys Tyr
            180                 185                 190

Gly Lys Lys Val Leu Ile Asn Leu Phe Val Gly Thr Asp Asp Lys Asn
        195                 200                 205

Ser Val Asn His Val Ile His Ile Asp Gln Pro Arg Leu Gly Leu Pro
    210                 215                 220

Ser Arg Asp Tyr Tyr Glu Cys Thr Gly Ile Tyr Lys Glu Ala Cys Thr
225                 230                 235                 240

Ala Tyr Val Asp Phe Met Ile Ser Val Ala Arg Leu Ile Arg Gln Glu
                245                 250                 255

Glu Arg Leu Pro Ile Asp Glu Asn Gln Leu Ala Leu Glu Met Asn Lys
            260                 265                 270

Val Met Glu Leu Glu Lys Glu Ile Ala Asn Ala Thr Ala Lys Pro Glu
        275                 280                 285

Asp Arg Asn Asp Pro Met Leu Leu Tyr Asn Lys Met Thr Leu Ala Gln
    290                 295                 300

Ile Gln Asn Asn Phe Ser Leu Glu Ile Asn Gly Lys Pro Phe Ser Trp
305                 310                 315                 320

Leu Asn Phe Thr Asn Glu Ile Met Ser Thr Val Asn Ile Ser Ile Thr
                325                 330                 335

Asn Glu Glu Asp Val Val Val Tyr Ala Pro Glu Tyr Leu Thr Lys Leu
            340                 345                 350

Lys Pro Ile Leu Thr Lys Tyr Ser Ala Arg Asp Leu Gln Asn Leu Met
        355                 360                 365

Ser Trp Arg Phe Ile Met Asp Leu Val Ser Ser Leu Ser Arg Thr Tyr
    370                 375                 380

Lys Glu Ser Arg Asn Ala Phe Arg Lys Ala Leu Tyr Gly Thr Thr Ser
```

```
                385                 390                 395                 400
Glu Thr Ala Thr Trp Arg Arg Cys Ala Asn Tyr Val Asn Gly Asn Met
                    405                 410                 415
Glu Asn Ala Val Gly Arg Leu Tyr Val Glu Ala Phe Ala Gly Glu
            420                 425                 430
Ser Lys His Val Val Glu Asp Leu Ile Ala Gln Ile Arg Glu Val Phe
        435                 440                 445
Ile Gln Thr Leu Asp Asp Leu Thr Trp Met Asp Ala Glu Thr Lys Lys
    450                 455                 460
Arg Ala Glu Glu Lys Ala Leu Ala Ile Lys Glu Arg Ile Gly Tyr Pro
465                 470                 475                 480
Asp Asp Ile Val Ser Asn Asp Asn Lys Leu Asn Asn Glu Tyr Leu Glu
                485                 490                 495
Leu Asn Tyr Lys Glu Asp Glu Tyr Phe Glu Asn Ile Ile Gln Asn Leu
            500                 505                 510
Lys Phe Ser Gln Ser Lys Gln Leu Lys Lys Leu Arg Glu Lys Val Asp
        515                 520                 525
Lys Asp Glu Trp Ile Ser Gly Ala Ala Val Val Asn Ala Phe Tyr Ser
    530                 535                 540
Ser Gly Arg Asn Gln Ile Val Phe Pro Ala Gly Ile Leu Gln Pro Pro
545                 550                 555                 560
Phe Phe Ser Ala Gln Gln Ser Asn Ser Leu Asn Tyr Gly Gly Ile Gly
                565                 570                 575
Met Val Ile Gly His Glu Ile Thr His Gly Phe Asp Asp Asn Gly Arg
            580                 585                 590
Asn Phe Asn Lys Asp Gly Asp Leu Val Asp Trp Trp Thr Gln Gln Ser
        595                 600                 605
Ala Ser Asn Phe Lys Glu Gln Ser Gln Cys Met Val Tyr Gln Tyr Gly
    610                 615                 620
Asn Phe Ser Trp Asp Leu Ala Gly Gly Gln His Leu Asn Gly Ile Asn
625                 630                 635                 640
Thr Leu Gly Glu Asn Ile Ala Asp Asn Gly Gly Leu Gly Gln Ala Tyr
                645                 650                 655
Arg Ala Tyr Gln Asn Tyr Ile Lys Lys Asn Gly Glu Glu Lys Leu Leu
            660                 665                 670
Pro Gly Leu Asp Leu Asn His Lys Gln Leu Phe Phe Leu Asn Phe Ala
        675                 680                 685
Gln Val Trp Cys Gly Thr Tyr Arg Pro Glu Tyr Ala Val Asn Ser Ile
    690                 695                 700
Lys Thr Asp Val His Ser Pro Gly Asn Phe Arg Ile Ile Gly Thr Leu
705                 710                 715                 720
Gln Asn Ser Ala Glu Phe Ser Glu Ala Phe His Cys Arg Lys Asn Ser
                725                 730                 735
Tyr Met Asn Pro Glu Lys Lys Cys Arg Val Trp
            740                 745
```

<210> SEQ ID NO 5
<211> LENGTH: 20
<212> TYPE: DNA
<213> ORGANISM: Artificial Sequence
<220> FEATURE:
<223> OTHER INFORMATION: Human PEX-specific primer

<400> SEQUENCE: 5
ggaggaattg gttgagggcg                                              20

<210> SEQ ID NO 6
<211> LENGTH: 20
<212> TYPE: DNA
<213> ORGANISM: Artificial Sequence
<220> FEATURE:
<223> OTHER INFORMATION: Human PEX-specific primer

<400> SEQUENCE: 6
gtagaccacc aaggatccag                                              20

<210> SEQ ID NO 7
<211> LENGTH: 24
<212> TYPE: DNA
<213> ORGANISM: Artificial Sequence
<220> FEATURE:
<223> OTHER INFORMATION: Human PEX-specific primer

<400> SEQUENCE: 7
cgtgcccaga actagggtgc cacc                                         24

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide PEX-4 used as primer

<400> SEQUENCE: 8
ctggatcctt ggtggtctac                                              20

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide PEX-5 used as primer

<400> SEQUENCE: 9
cactgtgcaa ctgtctcag                                               19

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide PEXMyc1 used as primer

<400> SEQUENCE: 10
ttggatgtca acgcctcg                                                18

<210> SEQ ID NO 11
<211> LENGTH: 70
<212> TYPE: DNA
<213> ORGANISM: Artificial Sequence
<220> FEATURE:
<223> OTHER INFORMATION: Oligonucleotide PEXMyc2 used as a primer

<400> SEQUENCE: 11
ctaccacaat ctacagttgt tcaggtcctc ttcgctaatc agcttttgtt ccatagagtc    60
catgcctctg                                                         70

INHIBITION OF PEX IN THE TREATMENT OF METABOLIC BONE DISEASES

CROSS-REFERENCE TO RELATED APPLICATIONS

This application is a continuation-in-part of and claims priority from U.S. application Ser. No. 09/806,110, which entered the US national phase on Mar. 28, 2001 based on PCT Application PCT/CA99/00895, filed on Sep. 27, 1999, which claims the benefit of priority from Canadian Patent Application No. 2,245,903 filed on Sep. 28, 1998, all of which are incorporated herein, in their entirety, by reference.

TECHNICAL FIELD

The invention relates to the use of PEX in the treatment of metabolic bone diseases, such as osteomalacia and osteoporosis.

BACKGROUND OF THE INVENTION

Mutations in the PEX (also known as PHEX) gene are responsible for X-linked hypophosphatemic rickets (HYP). To gain insight into the role of PEX in normal physiology we have cloned the human full-length cDNA and studied its tissue expression, subcellular localization, and peptidase activity. We show that the cDNA encodes a 749 amino acid protein structurally related to a family of neutral endopeptidases that include neprilysin (NEP) as prototype. By Northern blot analysis, the size of the full-length PEX transcript is 6.5 kb. PEX expression, as determined by semi-quantitative PCR, is high in bone and in tumor tissue associated with the paraneoplastic syndrome of renal phosphate wasting. PEX is glycosylated in the presence of canine microsomal membranes and partitions exclusively in the detergent phase from Triton X-114 extractions of transiently transfected COS cells. Immunofluorescence studies in A293 cells expressing PEX tagged with a c-myc epitope show a predominant cell-surface location for the protein with its C-terminal domain in the extracellular compartment, substantiating the assumption that PEX, like other members of the neutral endopeptidase family, is a type II integral membrane glycoprotein. Cell membranes from cultured COS cells transiently expressing PEX efficiently degrade exogenously added PTH-derived peptides, demonstrating for the first time that recombinant PEX can function as an endopeptidase. PEX peptidase activity may provide a convenient target for pharmacological intervention in states of altered phosphate homeostasis and in metabolic bone diseases.

X-linked hypophosphatemic rickets (HYP) is the most common inherited disorder of renal phosphate wasting characterized by severe hypophosphatemia, renal phosphate wasting, reduced serum concentrations of 1,25-dihydroxyvitamin D levels, and defective bone mineralization. Until recently, much of our understanding of HYP has been facilitated by the availability of two murine homologues, the Hyp and Gy mice, which exhibit many of the phenotypic features of HYP. Through positional cloning, however, a gene which spans the deleted region Xp22.1 in HYP patients, or is mutated in non-deletion patients with the disorder, was identified (designated PEX) and its partial cDNA sequence reported (The HYP Consortium (1995) *Nature Genetics* 11, 130-136). The predicted human PEX gene product, as well as its murine homologue (Du, L. et al. (1996) *Genomics* 36, 22-28), exhibit homology to a family of neutral endopeptidases involved in either activation or degradation of a number of peptide hormones. It has been postulated that PEX metabolizes a peptide hormone that modulates renal tubular phosphate handling. Such an activity could involve either the processing of a phosphate-reabsorbing hormone precursor to its active form or the inactivation of a circulating phosphaturic factor. These speculations notwithstanding, the physiologic function of the PEX gene product and the mechanisms that lead to the renal and skeletal abnormalities of HYP remain to be defined.

Oncogenous hypophosphatemic osteomalacia (OHO) is a rare acquired disorder of phosphate homeostasis with biochemical and physical abnormalities similar to HYP. This syndrome is associated with a variety of histologically distinct, usually benign, mesenchymal tumors whose excision promptly reverses the metabolic abnormalities and results in cure of the bone disease. It is generally thought that a factor(s) produced by these tumors promotes phosphaturia and inhibits the renal conversion of 25-hydroxyvitamin D to 1,25-dihydroxyvitamin D. The nature of the phosphaturic substance remains unknown and is likely distinct from both parathyroid hormone (PTH) and calcitonin, two polypeptide hormones known to inhibit the renal tubular reabsorption of phosphorus. Because of the striking similarity in the clinical presentation of patients with OHO and HYP, it is postulated that the factor causing phosphaturia in OHO is the active form of the PEX substrate. The identification and characterization of the putative PEX substrate, referred to as phosphatonin, however, will require first a better understanding of PEX function.

To date, there is still a need to understand how local factors produced in the bone regulate bone formation and bone resorption. Derangement of these factors leads to metabolic bone diseases. Pharmacological manipulation of such factors may serve as a novel approach to the treatment of these disorders.

It would be highly desirable to be provided with a tool in the treatment of metabolic bone diseases, such as osteomalacia and osteoporosis.

SUMMARY OF THE INVENTION

An aim of the present invention is to provide a tool in the treatment of metabolic bone diseases, such as osteomalacia and osteoporosis.

Another aim of the present invention is to provide the use of PEX in the treatment of metabolic bone diseases, such as osteomalacia and osteoporosis.

Another aim of the present invention is to provide a method of diagnostic of metabolic bone diseases, such as osteomalacia and osteoporosis.

Toward this objective, we have cloned a cDNA encoding the full-length human PEX protein, and determined the tissue distribution of PEX transcripts. In addition, we have examined the subcellular localization of recombinant PEX protein and demonstrated its peptidase activity.

In accordance with the present invention there is provided a method for the diagnosis of metabolic bone diseases in a patient, which comprises the step of determining the level of PTHrP in a biological sample of a patient wherein an alteration of PTHrP levels from that of a normal individual is indicative of metabolic bone diseases and/or metabolic bone diseases predisposition.

In accordance with the present invention there is provided a method for the treatment of metabolic bone diseases, which comprises administering to a patient a compound for the modulation of PEX enzymatic activity.

In accordance with the present invention there is provided the use of a compound for the modulation of PEX enzymatic activity for the manufacture of a medicament for treating metabolic bone diseases.

In accordance with the present invention there is provided a method for the treatment of metabolic bone diseases, which comprises modulating PTH and PTHrP levels that regulate osteoblast activity in a patient to modulate bone breakdown and bone formation.

In accordance with the present invention there is provided the use of a compound for the modulation of PTH and PTHrP levels that regulate osteoblast activity for the treatment of metabolic bone diseases.

In accordance with the present invention there is provided a non-human transgenic mammal to study the role of PEX in bone development and homeostasis, whose germ cells and somatic cells contain a PEX gene construct for expression of PEX in osteoblast consisting essentially of a recombinant PEX gene sequence under the control of a proximal promoter of a pro-al(I) collagen gene, the PEX gene construct being introduced into the mammal, or an ancestor of the mammal, at an embryonic stage.

The non-human mammal is preferably a mouse and the proximal promoter is preferably murine pro-al(I) collagen gene, more preferably a 2.3 kb fragment thereof.

For the purpose of the present invention the following terms are defined below.

The expression "metabolic bone diseases" includes, without limitation, osteomalacia, osteoporosis, osteopetrosis, Paget's disease and X-linked hypophosphatemic rickets.

The present invention provides a method for treating metabolic bone disease, said method comprising modulating PEX expression and/or PEX enzymatic activity. In a preferred embodiment, the modulation of PEX comprises the modulation of PTH and/or PTHrP levels in osteoblast microenvironment. In a preferred embodiment, the modulation of PEX comprises the inhibition of PEX activity by a compound; wherein said compound is any compound that inhibits PEX expression or PEX enzymatic activity. In a preferred embodiment, the compound allows for an increase in PTH/PTHrP levels in osteoblast microenvironment. In a preferred embodiment, the compound is selected from the group consisting of inhibitors of NEP and/or ECE and/or PEX such as phosphoramidon, phosphoramidon analogs, Zn chelators, such as O-phenanthroline, any peptides that are homologous to PTH (1-34), wherein said peptides comprise at least one aspartate residue, and small molecule peptidomimetic analogs thereof. In a preferred embodiment, the modulation of PTH/PTHrP comprises the modulation bone breakdown and/or bone formation.

The present invention also provides a method for treating metabolic bone disease, said method comprising modulating PTH and/or PTHrP levels in osteoblast microenvironment; In an embodiment, PEX modulates PTH and/or PTHrP levels. In a preferred embodiment, a PEX-modulating compound modulates PTH and/or PTHrP levels. In a preferred embodiment, the PEX-modulating compound inhibits PEX expression or enzymatic activity. In accordance with the method for treating metabolic bone disease, comprising modulating PTH and/or PTHrP levels in osteoblast microviornment, the method comprises an increase in PTH/PTHrP levels in osteoblast microenvironment. In a preferred embodiment, the method comprises the use of a PEX inhibitor. In accordance with an embodiment of the present invention, a PEX inhibitor is selected from the group consisting of inhibitors of NEP and/or ECE and/or PEX such as phosphoramidon, phosphoramidon analogs, Zn chelators, such as O-phenanthroline any peptides that are homologous to PTH (1-34), wherein said peptides comprise at least one aspartate residue, and small molecule peptidomimetic analogs thereof.

There is also provided a method for the modulation of PTH/PTHrP levels, comprising administering a compound that modulates PEX expression or PEX enzymatic activity in the osteoblast microenvironment in a patient having a metabolic bone disease.

Also provided is a method for the modulation of PTH and/or PTHrP levels comprising the administration of PEX, a functional equivalent thereof, or a modulator thereof. In a preferred embodiment, the modulation of PTH and/or PTHrP levels is used to treat metabolic bone disease.

The present invention provides a method for modulating PEX enzymatic activity to treat metabolic bone disease in a patient. In a preferred embodiment, the method comprises administering a PEX-modulating compound; wherein said compound may be selected from the group consisting of inhibitors of NEP and/or ECE and/or PEX such as phosphoramidon, phosphoramidon analogs, Zn chelators, such as O-phenanthroline any peptides that are homologous to PTH (1-34), wherein said peptides comprise at least one aspartate residue, and small molecule peptidomimetic analogs thereof. In a preferred embodiment, the PEX-modulating compound modulates PTH and/or PTHrP levels in osteoblast microenvironment. More preferably, the PEX-modulating compound inhibits PEX enzymatic activity. In accordance with the teachings of the present invention, the PEX-modulating compound increases PTH/PTHrP levels in osteoblast microenvironment.

The present invention also provides the use of a PEX inhibitor, or PEX modulator, for the treatment of metabolic bone disease. Also provided is the use of a PEX inhibitor, or PEX modulator for modulating PTH/PTHrP levels in osteoblast microenvironment. In accordance with said uses, the PEX inhibitor preferably increases PTH/PTHrP levels in osteoblast microenvironment.

The present invention also provides the use of a compound that inhibits or modulates PEX expression and/or PEX enzymatic activity for the treatment of metabolic bone disease. In a preferred embodiment, the compound is selected from the group consisting of inhibitors of NEP and/or ECE and/or PEX such as phosphoramidon, phosphoramidon analogs, Zn chelators, such as O-phenanthroline any peptides that are homologous to PTH (1-34), wherein said peptides comprise at least one aspartate residue, and small molecule peptidomimetic analogs thereof.

The present invention also provides a method for treating metabolic bone disease, said method comprising modulating PTH and/or PTHrP by administering PEX or a modulator thereof. In a preferred embodiment, PEX modulates PTH and/or PTHrP levels to modulate bone breakdown and/or bone formation.

The present invention additionally provides a method for the diagnosis of metabolic bone disease in a patient, which comprises the step of determining the level of PTHrP in a biological sample of a patient wherein an alteration of PTHrP levels from that of a normal individual is indicative of metabolic bone diseases and/or metabolic bone diseases predisposition.

Also provided is a method for the treatment of metabolic bone diseases, which comprises administering to a patient a compound for the modulation of PEX enzymatic activity which modulates PTH and PTHrP levels that regulate osteoblast activity.

There is also provided a method for the treatment of metabolic bone diseases, which comprises modulating PTH and PTHrP levels that regulate osteoblast activity in a patient to modulate bone breakdown and bone formation.

In a preferred embodiment, the present invention provides the use of a compound for the modulation of PEX enzymatic activity for the manufacture of a medicament for treating metabolic bone diseases, wherein said compound modulates PTH and PTHrP levels that regulate osteoblast activity. In another preferred embodiment, the use of a compound for the modulation of PTH and PTHrP levels that regulate osteoblast activity for the treatment of metabolic bone diseases is further provided.

In accordance with the present invention, metabolic bone diseases may be selected from, but not limited to, the group consisting of osteomalacia, osteoporosis, osteopetrosis, Paget's disease and X-linked hypophosphatemic rickets.

The present invention also provides a non-human transgenic mammal to study the role of PEX in bone development and homeostasis, whose germ cells and somatic cells contain a PEX gene construct for expression of PEX in osteoblast consisting essentially of a recombinant PEX gene sequence under the control of a proximal promoter of a pro-al(I) collagen gene, the PEX gene construct being introduced into the mammal, or an ancestor of the mammal, at an embryonic stage. In a preferred embodiment, the mammal is a mouse. In another embodiment, the proximal promoter is murine pro-al(I) collagen gene. In a preferred embodiment, the murine pro-al(I) collagen gene is a 2.3 kb fragment thereof.

The present invention also provides a pharmaceutical composition comprising a pharmaceutically effective amount of a compound selected from the group consisting of inhibitors of NEP and/or ECE and/or PEX such as phosphoramidon, phosphoramidon analogs, Zn chelators, such as O-phenanthroline any peptides that are homologous to PTH (1-34), wherein said peptides comprise at least one aspartate residue, and small molecule peptidomimetic analogs thereof for the treatment of metabolic bone disease. In a preferred embodiment, the pharmaceutical composition modulates, or inhibits, PEX expression and/or enzymatic activity. In another preferred embodiment, the pharmaceutical composition modulates PTH/PTHrP levels in osteoblast microenvironment.

The present invention also provides a compound selected from the group consisting of inhibitors of NEP and/or ECE and/or PEX such as phosphoramidon, phosphoramidon analogs, Zn chelators, such as O-phenanthroline, any peptides that are homologous to PTH (1-34), wherein said peptides comprise at least one aspartate residue, and small molecule peptidomimetic analogs thereof for the treatment of metabolic bone disease. In a preferred embodiment, said metabolic bone diseases is selected from the group consisting of osteomalacia, osteoporosis, osteopetrosis, Paget's disease and X-linked hypophosphatemic rickets.

In another embodiment, there is provided a compound that stimulates PEX expression and/or enzymatic activity to treat diseases comprises excessive PTH/PTHrP activity. In a preferred embodiment, said diseases comprises fibrous dysplasia, osteitis fibrosa cystica in patients with chronic renal failure, and other diseases comprising elevated levels of PTH/PTHrP.

The present invention also provides for the use of any compound or PEX-modulating compound of the present invention in the preparation of a medicament for the treatment of metabolic bone disease, or any diseases associated with abnormal levels of PTH/PTHrP or abnormal PTH/PTHrP activity.

The present invention also provides a method of identifying a compound that modulates PEX enzymatic activity, the method comprising: (i) contacting PEX with a substrate for PEX and a test compound; and (ii) determining whether degradation of the substrate is modulated in the presence of the test compound; wherein when degradation of the substrate is modulated said compound is identified as having a therapeutic potential for PEX modulation. In a preferred embodiment, said substrate is parathyroid hormone (PTH) and/or parathyroid hormone-related peptide (PTHrP). In a preferred embodiment, said modulation is a decrease in PEX enzymatic activity. In another preferred embodiment, said substrate is PTH and said modulatioin is an increase in PEX enzymatic activity. In an embodiment, the method of the present invention further comprises: (iii) selecting said compound as a candidate compound for treating metabolic bone disease in a mammal.

The present invention additionally provides a method for screening compounds capable of modulating PEX activity, said method comprising the steps of: (a) contacting a test compound a sample comprising PEX and a PEX substrate; (b) determining whether PEX activity on said PEX substrate is modulated in the presence of said test compound, wherein changes in PEX substrate levels are determined; (c) identifying said test compound as a potential modulator of PEX activity based on the result of step (b). In a preferred embodiment, changes in PEX substrate levels may be determined by measurement of degradation of said substrate by PEX in the presence of said test compound.

All references cited herein are incorporated herein by reference to the same extent as if each individual publication, patent application or issued patent was specifically and individually indicated to be incorporated by reference in its entirety for all purposes.

BRIEF DESCRIPTION OF THE DRAWINGS

Further features and advantages of the present invention will become apparent from the following detailed description, taken in combination with the appended drawings, in which:

FIG. 2A illustrates human PEX cDNA cloned from OHO tumors (SEQ ID NOS:1-2);

FIG. 2B illustrates human PEX and human NEP protein alignment (SEQ ID NOS:3-4);

FIG. 2C illustrates the TMpred output for PEX;

FIG. 3 illustrates PEX expression in human tissues;

FIG. 4 illustrates a Northern blot analysis of PEX mRNA;

FIG. 5 illustrates in vitro translation of human PEX cRNA;

FIGS. 6A-6C illustrate TRITON™ X-114 extraction and immunofluorescent localization of PEX;

FIGS. 7A-7C illustrate HPLC analysis of the hydrolysis of [D-Ala$^2$,Leu$^5$]enkephalin;

FIG. 9 illustrates Schematic representation of phosphate handling in the proximal renal tubule in normal, OHO, and HYP states;

DETAILED DESCRIPTION OF THE PREFERRED EMBODIMENT

PEX is a Cell Membrane-Associated Protein

Figure 1:
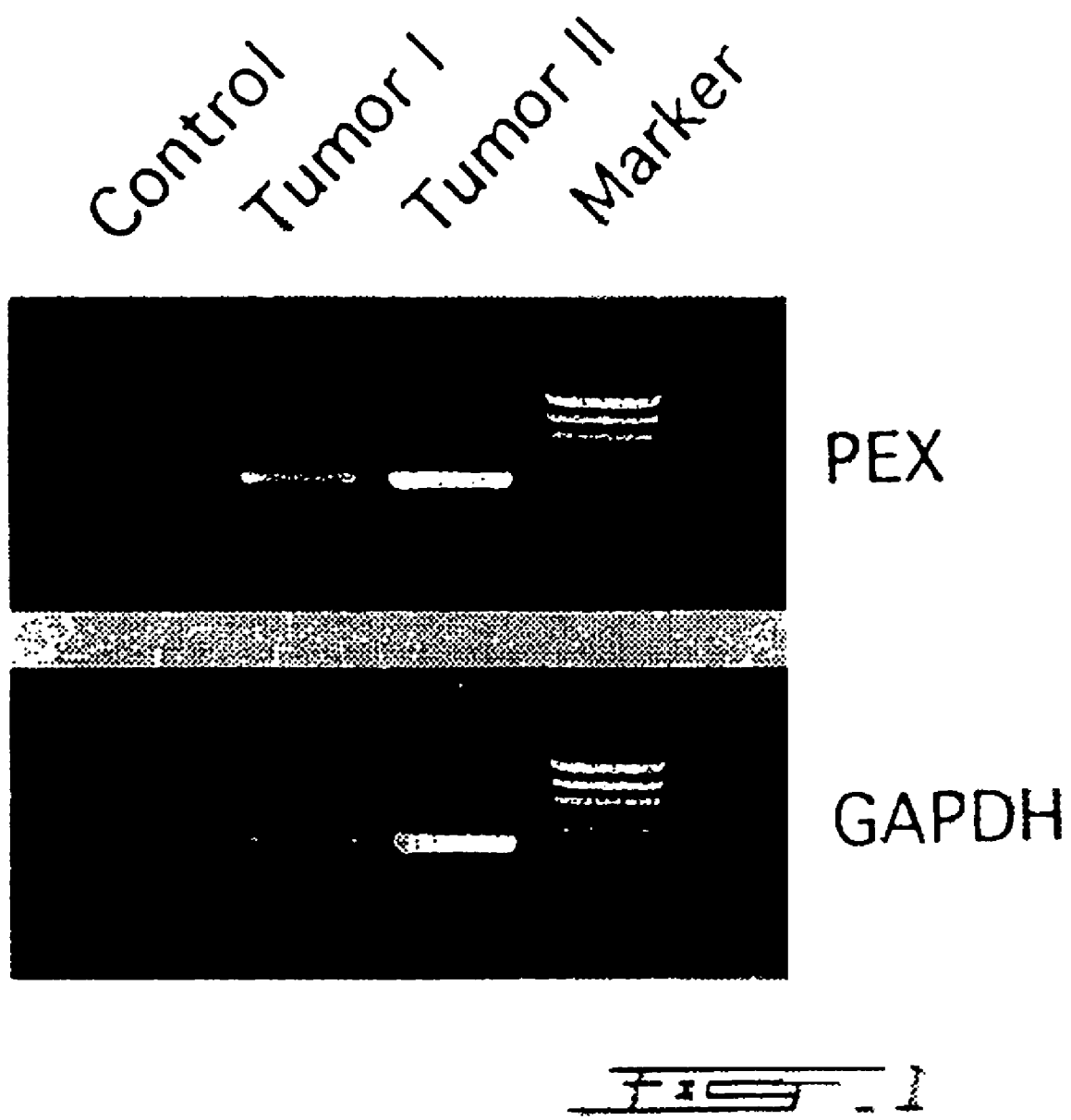
FIG. 1 illustrates PEX mRNA expression in OHO tumors.

Previous studies have established that NEP, ECE-1 and Kell blood group glycoprotein are integral membrane proteins. We have used extraction with the detergent TRITON™ X-114 and immunochemical localization to examine whether PEX is also a membrane-associated protein. For identification of PEX, we generated a construct in which the carboxyl terminus sequences of PEX are modified by a human c-myc tag. The epitope tag was inserted immediately upstream of the potential prenylation motif so that any lipid modification of the PEX protein may proceed uninterrupted.

TRITON™ X-114 is a detergent that forms an aqueous solution at 4° C. but separates into hydrophobic and aqueous phases when the temperature is raised to 30-37° C. This property has been used as an indicator of the hydrophobic nature of proteins, with integral membrane proteins partitioning exclusively in the detergent phase while highly hydrophilic proteins associate with the aqueous phase. TRITON™ X-114 extracts from COS-7 cells transiently expressing PEX tagged with the c-myc epitope showed that PEX partitions nearly exclusively into the detergent phase. This finding indicates that PEX is a membrane-associated protein and is consistent with the prediction from sequence analysis that it is an integral membrane protein.

To determine the subcellular localization of PEX, the distribution of recombinant protein expressed in stably transfected A293 cells was examined using immunofluorescence. When cells were fixed and permeabilized, myc-tagged PEX immunostaining was detected primarily on the cell surface, but in a number of cells staining was also observed intracellularly, although no signal was observed in the nucleus. If permeabilization was omitted, staining was localized exclusively to the plasma membrane, while untransfected cells or cells transfected with vector alone showed no immunofluorescent staining. Since the myc-tag was inserted in the carboxyl end of PEX, these findings further corroborate the sequence-based prediction that PEX is a Type II integral membrane protein with its large C-terminal hydrophilic domain containing the active enzymatic site in the extracellular compartment.

Recombinant PEX Protein has Peptidase Activity

The subcellular localization and sequence similarity between PEX and NEP strongly suggest that PEX functions as a membrane-bound metallopeptidase. However, no peptidase activity has yet been ascribed to PEX. As shown, when [D-Ala$^2$, Leu$^5$] enkephalin, used to assay for NEP activity, was incubated with cell membrane preparations from vector-transfected COS cells or COS cells expressing equivalent amounts of recombinant human NEP or PEX proteins, as determined by Western blot analysis, production of Tyr-D-Ala-Gly from the substrate was evident only in NEP-expressing membrane preparations. While the PEX sequence preserves two of the residues critical for catalytic activity of NEP (equivalent to $E^{646}$ and $H^{711}$), it lacks a residue equivalent to $R^{102}$ shown to be crucial for the dipeptidylcarboxypeptidase activity of NEP. Therefore, unlike NEP, PEX has no dipeptidylcarboxypeptidase activity.

To test for peptidase activity of recombinant PEX, cell membrane preparations from vector-transfected COS cells or COS cells expressing recombinant PEX protein were incubated with human parathyroid hormone PTH (1-34) and PTH (1-38). As shown, PEX activity was able to degrade both peptides in a very characteristic pattern. Therefore, PEX functions as an endopeptidase, and more specifically we have shown for the first time that it degrades PTH. Accordingly, the present invention clearly provides that PTH (1-34) is the first and only known substrate of PEX in its native membrane bound form.

These observations are important in that it is shown that PEX is a membrane bound protein with its active enzymatic site in the extracellular compartment. The cells with the highest level of PEX expression are the osteoblasts (bone forming cells). These cells are also the site of action of circulating PTH at the level of the bone. PTH stimulates these cells to produce factors (nature unknown) which in turn stimulate other bone cells, specifically the osteoclasts, to break down bone. Since PEX likely inactivates PTH in contact with osteoblasts, it would result in decreased stimulation of osteoclasts and therefore less bone breakdown.

Alternatively, osteoblasts produce parathyroid hormone-related peptide, PTHrP, which is important in the development of normal bone density. PTHrP shares many of the structural features of PTH and, would also serve as a substrate for PEX, as would be understood by one skilled in the art. Our previous studies using PTHrP heterozygous-null mice generated by gene targeting have shown that decreased levels of PTHrP in the skeletal microenvironment lead to a premature form of osteoporosis. PEX in osteoblasts would likewise modulate local PTHrP levels and thus bone formation. Accordingly, inhibition of PEX enzymatic activity allows for higher local concentrations of PTH/PTHrP and therefore better bone formation.

By examining PTH breakdown fragments, we can now design peptide and non-peptide activators and inhibitors of PEX enzymatic activity.

By modulating PTH and PTHrP levels that regulate osteoblast activity, PEX plays a critical role in the pathogenesis of osteomalacia and osteoporosis. By pharmacological modulation of PEX activity, it will be possible to modulate bone breakdown and bone formation, thereby providing a completely novel approach to the treatment of these metabolic bone diseases.

Experimental Procedures

Tumor Tissues

Patient I was a 55 year-old woman who presented with a two-year history of progressively increasing bone pain and difficulty in walking. X-rays of the lumbosacral spine showed diffuse osteopenia. Biochemical investigation showed the serum calcium level to be normal while serum phosphorus was low (0.41 to 0.57 mmol/L; normal, 0.8-1.6 mmol/L). Alkaline phosphatase was 232 U/L (normal, 30-105 U/L) and tubular reabsorption of phosphate while the patient was hypophosphatemic was decreased to 63% (normal, >80%). A search for a tumor was negative and the patient was treated with 1,25-dihydroxyvitaminD3 and oral phosphate. Five years later a right hand mass was discovered and was surgically removed. On histopathological examination, it was a fibrous hemangioma. Postoperatively, the patient noted increasing strength in her lower extremities and marked decrease in her pain. The serum phosphorus normalized (0.96 mmol/L) and the tubular reabsorption of phosphate improved but did not completely normalize (71-76%). No recurrence of the tumor has been found ten years later.

Patient II was a 21 year old man with classic features of OHO. Resection of a benign extraskeletal chondroma from the plantar surface of the foot resulted in complete reversal of the biochemical and clinical abnormalities associated with the syndrome.

Tumor tissue obtained from these two patients at surgery was frozen immediately in liquid nitrogen and stored at −70° C.

PEX Expression in OHO-Associated Tumors

RNA was extracted from tumor tissue using the RNeasy™ Total RNA kit (Qiagen, Chatsworth, Calif.) and reverse transcribed using oligo(dT) primer and Superscript II (BRL) reverse transcriptase for 1 hour at 42° C. in a final reaction volume of 30 µl. The resulting cDNA was then amplified using human PEX-specific oligonucleotide primers PEX-1 (5'-GGAGGAATTGGTTGAGGGCG-3' SEQ ID NO:5) and PEX-2 (5'-GTAGACCACCAAGGATCCAG-3' SEQ ID. NO:6), designed from the published cDNA sequence (1298 and 1807 are the nucleotide positions of the 5' end of the sense and antisense primers, respectively) (The HYP Consortium (1995) *Nature Genetics* 11, 130-136). Following amplification (35 cycles), an aliquot of the PCR reaction was fractionated on an 1% agarose gel and visualized following staining with ethidium bromide.

Cloning of Full-Length PEX cDNA

Cloning of the 5' end of PEX cDNA was accomplished by anchored PCR. Total cellular RNA was extracted from tumor II and mRNA was prepared. 1.5 µg of mRNA was reverse transcribed into cDNA using 100 ng of a PEX-specific antisense oligomer (PEX-2) and 200 units of Superscript II (BRL) reverse transcriptase for 1 hour at 42° C. in a final reaction volume of 30 µl. The resulting cDNA was size fractionated on a 1% agarose gel and fragments corresponding to >600 bp were purified and resuspended in $H_2O$. The 3' end of the first strand cDNA was homopolymer tailed with dGTP using 1 µl of Terminal deoxynucleotidyl transferase (TdT) at 37° C. for 30 minutes in a volume of 50 µl. Following heat inactivation of the enzyme, the RNA template was removed by incubation with RNase H and the tailed cDNA was purified by phenol-chloroform extraction followed by ammonium acetate precipitation. The purified tailed cDNA was resuspended in $H_2O$ and an aliquot was used for anchored PCR analysis along with 200 ng of an internal PEX specific antisense primer (PEX-3,5'-CGTGCCCAGAACTAGGGT-GCCACC-3' (SEQ ID NO:7); nucleotide 98 of the published human cDNA sequence is the 5' end of the primer) and 200 ng of oligodC as the sense primer. Forty cycles of PCR were performed using 0.5 µl of Taq polymerase (Promega Biotec, Madison, Wis.) in a reaction volume of 50 µl. Cycling parameters were: 1 minute of denaturation at 94° C., 2 minutes of annealing at 55° C. and 2 minutes of extension at 72° C. The PCR products were fractionated on a 1% agarose gel and a band of 700 bp was isolated, purified, and ligated into pPCRII vector (Invitrogen). Following transformation into INVαF' bacteria, clones containing the appropriate size insert were sequenced.

To clone the 3' end of PEX cDNA, an aliquot of an amplified unidirectional cDNA library in pcDNA3 vector (Invitrogen) generated from mRNA obtained from tumor I was grown overnight in LB medium and plasmid DNA extracted. DNA (0.5 µg) was subjected to PCR using a PEX-specific sense oligomer (PEX-1) and an antisense oligomer corresponding to the SP6 RNA polymerase binding site sequences present in the pcDNA3 vector. Thirty-five cycles of amplification were performed in a 50 µl reaction volume with each cycle consisting of 1 min denaturation at 94° C., 1 min annealing at 55° C. and 1 min extension at 72° C. Amplified products were fractionated on a 1% agarose gel and a 1.2 kb fragment corresponding to the 3' end of PEX cDNA was subcloned and sequenced.

For expression studies, an EcoRV (in the polylinker of pPCRII)/AccI (in the PEX sequence) fragment containing the 5' end of PEX cDNA was ligated into the pPCRII vector containing the 3' end of PEX cDNA following digestion with AccI and EcoRV. The resulting plasmid was restricted with KpnI and NotI excising the full length PEX cDNA that was then inserted into pcDNA3 vector digested at the KpnI/NotI sites in the polylinker region, resulting in plasmid pPEX. The full-length PEX cDNA was sequenced using an Applied Biosystems 373A automated sequencer.

Tissue Expression of PEX mRNA

PEX expression was examined in normal human tissues and in the Saos-2 human osteoblastic osteosarcoma cell line, by RT-PCR using oligonucleotides PEX-4 (5'-CTGGATC-CTTGGTGGTCTAC-3' SEQ ID NO:8) and PEX-5 (5'-CACTGTGCAACTGTCTCAG-3' SEQ ID NO:9) as sense and antisense primers (2398 and 2895 are the nucleotide positions of the 5' end of these primers designed from the full-length human PEX cDNA). Semiquantitative PCR analysis for PEX expression in human tissues was performed as previously described, following normalization for GAPDH message in all samples containing PEX transcripts.

Northern-blot Analysis

Total RNA was obtained from Tumor I and human Saos-2 osteosarcoma cells using the RNeasy Total RNA kit (Qiagen) and oligo(dT)-purified poly(A)$^+$ RNA was isolated from Saos-2 total RNA using standard procedures. Twenty micrograms of Tumor I total RNA and 20 µg of Saos-2 poly(A)$^+$ RNA were fractionated on 1% denaturing agarose gel, and transferred to nylon membrane (Hybond N$^+$, Amersham). Hybridization was performed with $^{32}$P-labeled full-length human PEX cDNA (3.1 kb) in 7 mM Tris-HCl, 50% formamide, 10% dextran sulfate, 4×SSC, 2× Denhardt's solution and heat-denatured salmon sperm DNA (100 µg/ml). The blot was washed in 0.1×SSC, 0.1% SDS for 20 min at 50° C., and subjected to autoradiography for 4 days.

In Vitro Transcription, Translation, and Analysis of Products

Plasmid pPEX was linearized with NotI and sense RNA strand was transcribed using T7 RNA polymerase. Translation reactions in rabbit reticulocyte lysate were performed in the presence of [$^3$H]leucine according to the manufacturer's recommendations (Promega) with or without canine pancreas microsomal membranes. Products were analyzed by SDS-polyacrylamide gel electrophoresis (SDS-PAGE; 8%). Autoradiography was performed after treating the gel with EN$^3$HANCE (Dupont NEN), as previously described.

Generation of Myc-tagged PEX, Transfection in COS-7 Cells, and Triton X-114 Extraction Plasmid pPEX-myc was generated by PCR amplification of PEX cDNA using oligonucleotide PEXMyc1 as the sense primer (5'-TTGGATGTCAACGCCTCG-3' SEQ ID NO:10, 519 is the nucleotide position of the 5' end of this primer designed from the cloned human PEX cDNA) and PEXMyc2 as the antisense (5'-CTACCACAATCTACAGTTGTTCAG-GTCCTCTTCGCTAATCAGCTTTTGTTC-CATAGAGTCCATGCCTCTG-3' SEQ ID NO:11) primer. The latter encodes the human c-myc tag sequences (underlined) and PEX sequences corresponding to the carboxyl terminal of the mature protein ($^{742}$RGMD SMEQKLISEEDLNNCRLW* (SEQ ID NO: 12)). Following PCR, the amplified fragment was ligated to the pPCR II vector, excised by digestion with KpnI/NotI and inserted into the corresponding sites in the polylinker region of pcDNA3. The in-frame fusion protein was verified by DNA sequencing.

COS-7 cells maintained in Dulbecco's modified Eagle's medium (DMEM, 4,500 mg/L glucose with L-glutamine; JRH Biosciences, Lenexa, Kans.) supplemented with 10% fetal calf serum (FCS; GIBCO) and antibiotics (pen/strep) were plated at a density of 3×10⁵ cells/well in 6-well cluster plates 24 h prior to transfection. Cells were washed with twice with PBS and incubated with 2 μg of pPEX-myc plasmid DNA in 1 ml of DMEM containing 0.1% BSA, and DEAE-dextran (Pharmacia LKB) for 3.5 h at 37° C. Following incubation, the transfection medium was aspirated, the cells were shocked with 10% DMSO in PBS for 2 min, and then cultured in DMEM with 10% calf serum at 37° C. for 48 h. Triton X-114 extraction were performed on cultured cells expressing myc-tagged PEX as described. The samples were then analyzed by immunoblotting using the 9E10 anti-myc monoclonal antibody.

Stable Transfection of A293 Cells and Immunofluorescence

A293 cells maintained in DMEM with 10% FCS were transfected with the pPEX-myc plasmid by electroporation and selection initiated using G418 (600 mg/ml for 14 days and then decreased to 400 mg/ml). Populations of stably transfected cells were recovered at the end of the selection period. For myc-tagged PEX indirect immunofluorescence, stably transfected cells plated on gelatin-coated coverslips were washed twice with PBS, fixed in 4% parafolmaldehyde and in some experiments permeabilized with 0.5% Triton X-100. Cells were blocked with 10% FCS in DMEM for 30 min, washed and incubated for 1 hr at 37° C. with the 9E10 anti-myc monoclonal antibody (1:500 dilution). Cells were subsequently washed and incubated in turn with fluorescein-conjugated sheep anti-mouse secondary antibody (1:250 dilution). Coverslips were rinsed extensively with PBS, mounted in medium (glycerol:Tris; 1:1) containing 2.5% 1,4-diazabicyclo-(2,2,2) octane (Sigma) and examined with fluorescent microscopy using appropriate filters.

Assay for Membrane-bound Endopeptidase Activity

COS-7 cells transiently transfected with pcDNA3 vector alone, with vector containing human NEP cDNA (generous gift of P. Crine, Université de Montréal), or with pPEX plasmid, were washed and scraped in PBS. Following brief centrifugation, the cell pellets were resuspended in 50 mM Tris-HCl, pH 7.4 and disrupted by sonication. Homogenates were fractionated by sequential centrifugation at 1,000×g for 10 min and then at 100,000×g for 60 min. The final precipitate was washed with 50 mM Tris-HCl, pH 7.4, resuspended in the same buffer, and assayed for endopeptidase activity. The protein concentration in membrane fractions was determined by the method of Bradford with bovine serum albumin as standard.

[D-Ala², Leu⁵] enkephalin (500 μM) was incubated with COS cell membrane preparations (~60 μg of protein) in 100 mM Tris-HCl, pH 7.0, at 37° C. for 30 min (final volume 30 μl). The reaction was terminated by the addition of 100 μl 0.1% TFA (v/v). Production of Tyr-D-Ala-Gly was monitored using reversed-phase HPLC (Bondpak C-18 reverse phase column, Waters) with a U.V. detector set at 214 nm. A linear solvent gradient of 0% B to 40% B in 60 min was used with a flow rate of 1.5 ml/min (mobile phase A=0.1% TFA (v/v); mobile phase B=80% acetonitrile/0.1% TFA). Tyr-D-Ala-Gly was identified by co-chromatography with marker synthetic peptide. For assessing PEX endopeptidase activity, 10 μg of PTH [1-38] and PTH [1-34] peptides (Peninsula Laboratories; Belmont, Calif.) were added to the membrane preparations. For HPLC analysis of hydrolysis products, a linear solvent gradient of 0% to 50% solution B was used at a rate of 1.5 ml/min. MALDI-TOF mass spectrometry was performed on specific peptide fragments.

Results

Cloning of Human PEX cDNA

At the initiation of these studies, PEX expression had been reported in minute amounts only in leukocytes and fetal brain. We postulated that in states of hypophosphatemia PEX expression may be increased and therefore opted to use the OHO tumor as a tissue source that may express considerably more PEX. Tissues obtained from two tumors associated with OHO were used to obtain total RNA and analysis for PEX mRNA expression was assessed by RT-PCR. As shown in FIG. 1, PEX transcripts were readily amplified from both tumor samples demonstrating the expected 509 bp fragment predicted from the published partial human PEX sequence (The HYP Consortium (1995) *Nature Genetics* 11, 130-136). Total RNA extracted from two tumors associated with OHO was reverse transcribed and amplified by PCR (35 cycles) using human PEX-specific primers, PEX-1 and PEX-2, designed from the published human sequence. The expected 509 bp amplified fragment was obtained from both tumor samples. Control, no cDNA added to the amplification reaction, i.e. negative control; Marker, Φ174 DNA digested with HaeIII restriction endonuclease.

The cloning of the 3' end of PEX transcript was performed by rapid amplification of the 3' end of the cDNA (3' RACE), while the 5' of the cDNA was amplified by anchored PCR, as described in Experimental Procedures. FIG. 2A shows the nucleotide and predicted amino acid sequence of the full-length human PEX cDNA cloned from tumor tissues. Nucleotide and deduced amino acid sequence of tumor-derived human PEX cDNA (FIG. 2A). The numbering begins at the 5' end nucleotide as determined by anchored PCR. Amino acids are given below each codon using the single letter code. The putative start codon is indicated as /1 along with the deduced amino acid translation. Two stop codons preceding the predicted initiation ATG are in bold type. Asterisk (*) indicates an in-frame stop codon, while a large asterisk ([) denotes the putative prenylation site. A potential polyadenylation signal in the 3' untranslated region is underlined. Nine potential N-glycosylation sites are boxed. The sequence has been assigned GenBank accession No. (U82970).

The composite cDNA reveals a single open reading frame encoding a protein of 749 amino acids which displays homology (34.2% identity, 70% similarity) to human neprilysin (NEP; EC 3.4.24.11), and other members of the membrane-bound metalloendopeptidase family encompassing endothelin-converting enzyme-1 (ECE-1; 66% similarity) and the Kell antigen (60% similarity), suggesting that PEX is a novel member of this family of neutral endopeptidases, as previously suggested (The HYP Consortium (1995) *Nature Genetics* 11, 130-136). Like the other members, PEX is a likely a glycoprotein with eight potential N-glycosylation sites and 10 cysteine residues that may be important for the proper folding and hence native conformation of the protein.

The ATG codon at position 604 was assigned as the initiator methionine since it is preceded by two in-frame TGA termination codons 36 and 63 basepairs upstream and conforms favorably to the Kozak consensus for vertebrate initiation of translation. The cloned cDNA identifies the first 3 and the last 108 amino acids of the predicted PEX gene product in addition to the published partial sequence. These additional amino acids comprise residues such as $E^{642}$ and $H^{710}$ that are shared by NEP, and may be critical for the formation of the active site of the protein and hence its enzymatic activity.

Three amino acid residues predicted from our cDNA clone differ from the published partial human PEX sequence, D363A (GAC to GCC), R403W (AGG to TGG), and A641G (GCG to GGA). To confirm that these alterations did not arise because of PCR errors, PEX sequences were amplified from Saos-2 human osteosarcoma cells (see below) and sequenced. In addition, the same alterations were subsequently described in the murine PEX cDNA, suggesting possible cloning artifacts in the published partial human PEX sequence. Our cloned sequences also encompass 603 nucleotides of the 5' untranslated region, and 276 nucleotides of the 3' untranslated region, including the canonical polyadenylation signal AATAAA, 19 nt upstream of the poly(A) tract. The human and the published mouse PEX cDNA sequences share extensive homology within the protein coding region (96% identity) as well as in the 5' and 3' non coding regions.

TMpred analysis of the human PEX sequence predicts that the protein has no apparent N-terminal signal sequence but has a single membrane-spanning helical domain comprising amino acid residues 21-39 (FIG. 2C). TMpred analysis of the PEX sequence showing a single membrane-spanning domain encompassing amino acid residues 21-39 (arrowhead). Numbers on the horizontal axis refer to the amino acid sequence. Amino acid homology between PEX and human NEP cDNA (FIG. 2B). Sequence comparison was performed using the LALIGN program.

This predicts its transmembrane topology to be that of a type II integral membrane protein with a 20-residue N-terminal cytoplasmic tail and a C-terminal of 700 amino acid residues containing the catalytic domain in the extracellular compartment. Unexpectantly, a CXXX box motif comprising amino acid residues $^{746}$CRLW was also identified at the carboxyl terminus of PEX. This motif may serve as a site for prenylation, a post-translational lipid modification involved in a number of processes including facilitating membrane attachment, targeting of proteins to specific subcellular membrane compartments, promoting protein-protein interactions and regulating protein function.

Accordingly, the use of cloned PEX cDNA confirms the size of PEX, PEX's trans-membrane localization on osteoblasts, PEX's homology with Neprilysin, PEX's almost exclusive expression in osteoblasts, as well as PEX's peptidase activity, as shown for the first time in the present application, wherein PEX acts as a peptidase, and is shown to cleave PTH(1-34).

Tissue Expression of PEX RNA

We next examined PEX expression in a number of fetal and adult tissues and compared the level of expression to OHO tumor RNA using semi-quantitative RT-PCR (FIG. 3). Quantitative RT-PCR amplification of the PEX transcripts from total RNA prepared from human tissues and OHO-associated tumor. Relative expression levels for the PEX transcript were measured by quantifying PEX product in reversed-transcribed RNA samples that have been previously normalized for GAPDH levels. The specific primers used were as follows: for PEX, the forward primer was PEX-4 and the reverse primer PEX-5; for GAPDH, the primers were as previously described. PCR products were electrophoresed on a 1.5% agarose gel and stained with ethidium bromide. Control, negative control; Marker, Φ174 DNA digested with HaeIII restriction endonuclease. Below, shown are the relative levels of PEX transcripts in various human tissues compared to those in the tumor.

PEX transcripts were expressed in human fetal calvarium and to a lesser degree in fetal kidney and skeletal muscle while no expression was apparent in fetal liver. PEX expression was also observed in the human osteoblastic osteosarcoma cell line, Saos-2. In adult tissues, PEX mRNA was identified in kidney, but not in liver, or endomyocardium. Recent studies have also reported PEX expression in human fetal bone, skeletal muscle, and liver as well as fetal and adult ovary and lung (Beck, L. et al. (1997) *J. Clin. Invest.* 99, 1200-1209; Grieff, M. et al. (1997) *Biochem. Biophys. Res. Commun.* 231, 635-639). Analysis following normalization for GAPDH message in all tissues containing PEX transcript disclosed that bone PEX expression is 2-10 fold higher than in other normal tissues examined. In comparison, OHO tumor PEX expression was twice the levels observed in fetal calvarium, consistent with its relative "overabundance" in these tissues.

Northern Blot Analysis

To determine the size of the full-length PEX transcript, we isolated total RNA from tumor I (quantity of available tissue was insufficient for poly(A)$^+$ RNA extraction) and poly(A)$^+$ RNA from human Saos-2 osteosarcoma cells. This cell line was used since it is readily available and successful amplification of PEX sequences has been performed by RT-PCR (see above). Aliquots (20 µg of each) were examined by Northern-blot analysis using the cloned human PEX cDNA as probe. A single transcript of approximately 6.5 kb was readily detected only in the Saos-2-derived poly(A)$^+$sample and contrasts with the predicted size of the cloned sequence of 3.1 kb (FIG. 4). Approximately 20 µg of poly(A$^+$)RNA prepared from Saos-2 cells and 20 µg of total RNA prepared from tumor I tissue were resolved on 1% agarose gel containing formaldehyde and then transferred to a nylon membrane. Following hybridization with radiolabeled PEX cDNA, the blot was washed and the signal detected by autoradiography. A transcript of ~6.5 kb was observed only in the lane containing Saos-2 poly(A$^+$)RNA. There is suggestion of an additional band corresponding to a transcript of ~3.8 kb. Arrows indicate the position of the 28 S (approx. 4.8 kb) and 18 S (approx. 1.8 kb) ribosomal RNA.

This finding would therefore predict a ~4 kb 5' untranslated region for PEX cDNA, consistent with published data from Northern blot analysis of PEX expression in mouse calvaria (Du, L. et al. (1996) *Genomics* 36, 22-28). A less well defined band was also detected in the Saos-2 sample corresponding to a potential transcript of ~3.8 kb, although the nature of this transcript remains unclear. Northern analysis of total RNA samples from tumor I and Saos-2 cells (results not shown) did not reveal any signal for PEX, consistent with the relatively low expression levels of the PEX transcript, previously described (The HYP Consortium (1995) *Nature Genetics* 11, 130-136; Beck, L. et al. (1997) *J. Clin. Invest.* 99, 1200-1209; Grieff, M. et al. (1997) *Biochem. Biophys. Res. Commun.* 231, 635-639). This finding contrasts sharply with PEX expression levels demonstrated in murine calvaria and cultured osteoblasts (Du, L. et al. (1996) *Genomics* 36, 22-28) and may reflect tissue and species differences.

In Vitro Translation of PEX cRNA

In vitro translation studies using full-length human. PEX cRNA were performed in the rabbit reticulocyte lysate cell-free system. In the absence of microsomal membranes, PEX cRNA was translated into an _86 kD protein, as predicted from the cloned cDNA sequence (FIG. 5). Plasmid pPEX was linearized and sense RNA strand transcribed using T7 RNA polymerase. Translation of PEX cRNA was performed using rabbit reticulocyte lysate in the absence (minus) and presence (plus) of canine pancreas rough microsomes. Products were electrophoresed in a SDS-polyacrylamide gel (10%) and visualized by autoradiography. Arrowhead in lane 2 indicates full-length human PEX protein. The addition of microsomal membranes results in the appearance of higher molecular weight forms that likely represent glycosylated products.

Following addition of canine microsomal membranes to the translation mixture, products of higher molecular weight (~100 kD) became apparent, consistent with N-glycosylation of PEX at the eight potential glycosylation sites deduced from the predicted sequence.

PEX is a Cell Membrane-Associated Protein

Previous studies have established that NEP, ECE-1 and Kell blood group glycoprotein are integral membrane proteins. We have used extraction with the detergent Triton X-114 and immunofluorescent localization to examine whether PEX is also a membrane-associated protein. For identification of PEX, we generated a construct in which the carboxyl terminus sequences of PEX are modified by a human c-myc tag. The epitope tag was inserted immediately upstream of the putative prenylation motif so that any potential lipid modification of the PEX protein may proceed uninterrupted.

Triton X-114 is a detergent that forms an aqueous solution at 4° C. but separates into hydrophobic and aqueous phases when the temperature is raised to 30-37° C. This property has been used as an indicator of the hydrophobic nature of proteins, with integral membrane proteins partitioning exclusively in the detergent phase while highly hydrophilic proteins associate with the aqueous phase. Triton X-114 extracts from COS-7 cells transiently expressing PEX tagged with the c-myc epitope showed that PEX partitions nearly exclusively into the detergent phase (FIG. 6A). Extraction and partitioning of PEX expressed in COS-7 cells with Triton X-114 (FIG. 6A). Plasmid pPEX-myc was transiently transfected in COS-7 cells and 48 h later cells were extracted with Triton X-114. Whole cell extracts, as well as detergent and aqueous phases, were analyzed by SDS-PAGE and immunoblotted with an anti-myc monoclonal antibody. Right margin indicates $M_r \times 10^{-3}$.

This finding indicates that PEX is a membrane-associated protein and is consistent with the prediction from sequence analysis that it is an integral membrane protein.

To determine the subcellular localization of PEX, the distribution of recombinant protein expressed in stably transfected A293 cells was examined using immunofluorescence. When cells were fixed and permeabilized, myc-tagged PEX immunostaining was detected primarily on the cell surface, but in a number of cells staining was also observed intracellularly, although no signal was observed in the nucleus (FIG. 6B). If permeabilization was omitted, staining was localized exclusively to the plasma membrane (FIG. 6C), while untransfected cells or cells transfected with vector alone showed no immunofluorescent staining. Localization of PEX using indirect immunofluorescence in stably transfected A293 cells with (FIG. 6B) and without (FIG. 6C) permeabilization with Triton X-100, respectively. Staining was carried out using the 9E10 anti-myc monoclonal antibody, followed by fluorescein-labeled secondary (sheep anti-mouse) antibody. Arrowheads indicate intracellular (B) and plasma membrane staining (C).

Since the myc-tag was inserted in the carboxyl end of PEX, these findings further corroborate the sequence-based prediction that PEX is a type II integral membrane protein with its large C-terminal hydrophilic domain in the extracellular compartment.

Recombinant PEX Protein has Endopeptidase Activity

Figure 7C:
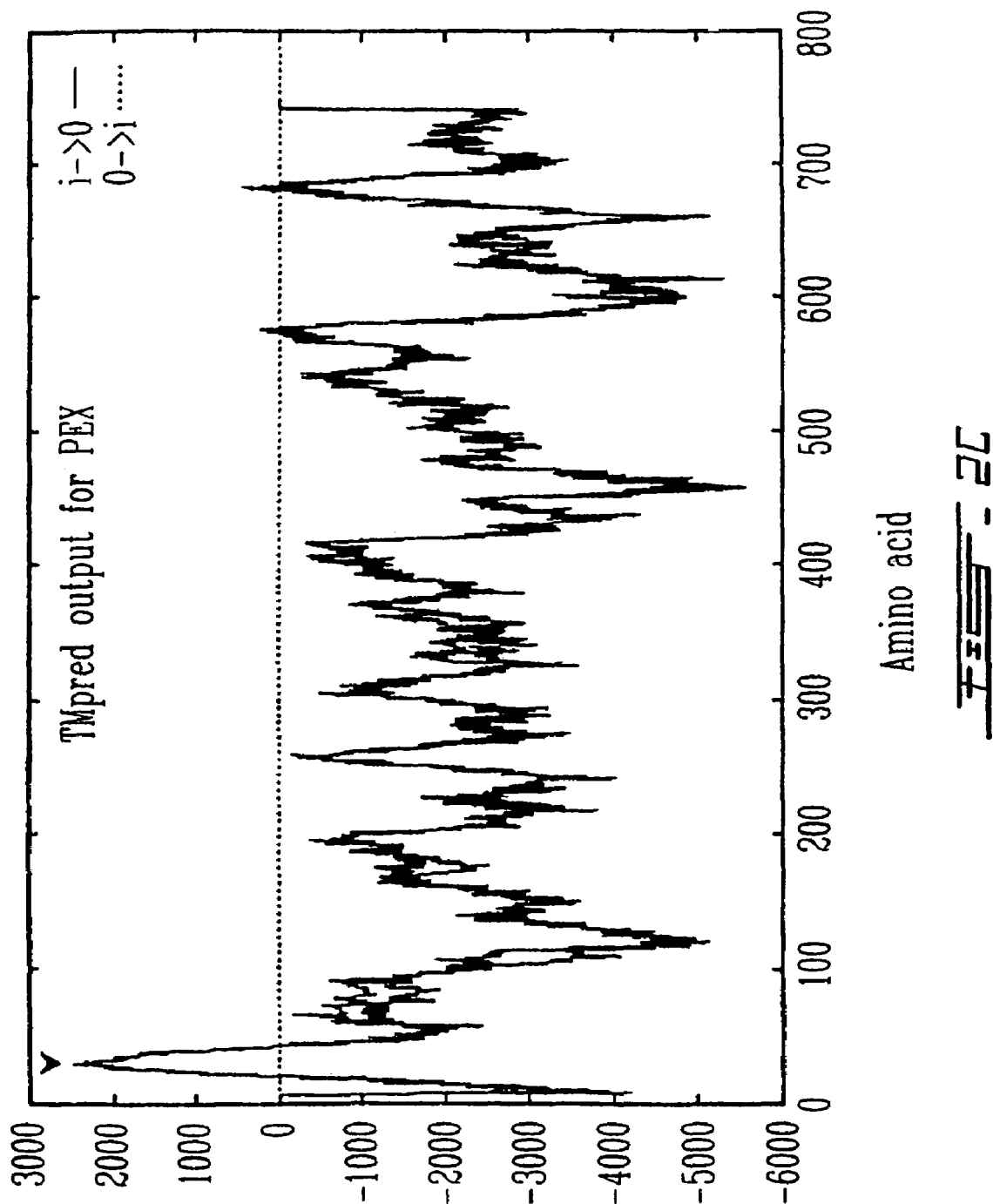

The subcellular localization and sequence similarity between PEX and NEP strongly suggest that PEX functions as a membrane-bound metallopeptidase. However, no peptidase activity has been ascribed to PEX. As shown in FIG. 7A, when [D-Ala$^2$, Leu$^5$] enkephalin, used to assay for NEP activity, was incubated with cell membrane preparations from vector-transfected COS cells or COS cells expressing equivalent amounts of recombinant human NEP or PEX proteins, as determined by Western blot analysis, production of Tyr-D-Ala-Gly from the substrate was evident only in NEP-expressing membrane preparations. Cell membrane preparations from vector transfected COS-7 cells (FIG. 7A) or from cells transiently expressing human NEP (FIG. 7B) or, human PEX cDNAs (FIG. 7C) were incubated in the presence of [D-Ala$^2$, Leu$^5$]enkephalin (500 μM) and hydrolysis products were resolved by HPLC as described in the Experimental Procedures section. Tyr-D-Ala-Gly was identified by chromatography of synthetic marker peptide.

While the PEX sequence preserves two of the residues critical for catalytic activity of NEP (equivalent to $E^{646}$ and $H^{711}$), it lacks a residue equivalent to $R^{102}$ shown to be crucial for the dipeptidylcarboxypeptidase activity of NEP. Therefore, unlike NEP, PEX has no dipeptidylcarboxypeptidase activity, but functions as an endopeptidase.

Figures 8A, 8B, 8C:
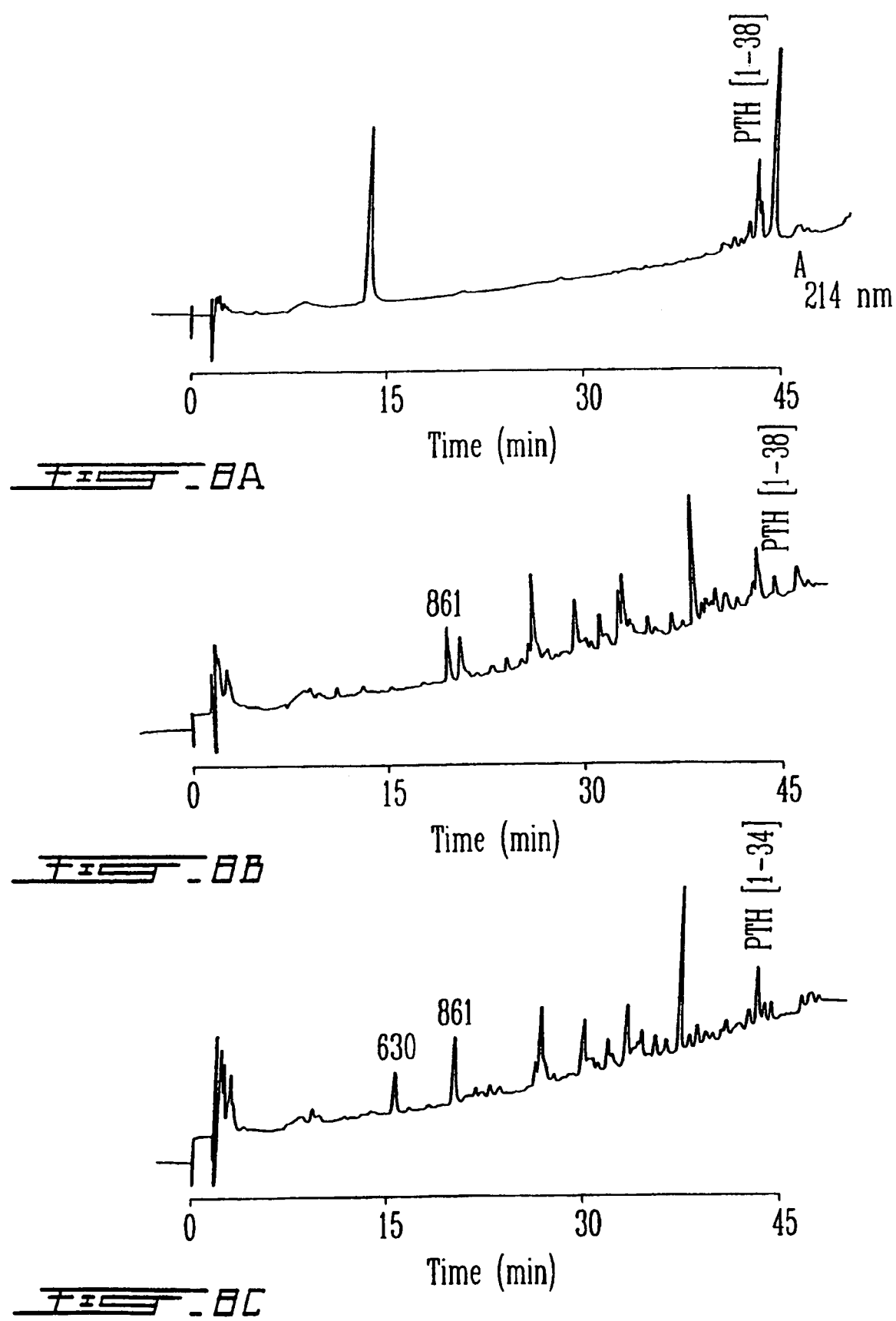
FIGS. 8A-8C illustrate the hydrolysis of PTH-derived peptides by PEX endopeptidase activity.

To examine recombinant human PEX for endopeptidase activity, cell membrane preparations from COS cells transiently expressing the protein were incubated with human PTH [1-38] or PTH [1-34] and the cleavage products were analyzed by reverse-phase high pressure liquid chromatography (HPLC), as shown in FIG. 8. Human PTH [1-38] was incubated with cell membrane preparations from vector transfected COS-7 cells (FIG. 8A) or from cells transiently expressing human PEX and hydrolysis products were resolved by HPLC (FIG. 8B). Chromatographic profile of products arising from the hydrolysis of PTH [1-34] when incubated with cell membranes from COS-7 cells transiently expressing PEX (FIG. 8C). The novel product with a molecular weight of 630 likely corresponds to the terminal pentapeptide DVHNF of human PTH [1-34].

A parallel preparation from vector transfected COS cells did not appreciably cleave PTH [1-38]. However, in the presence of PEX, both PTH peptides were hydrolyzed in a highly reproducible pattern resulting in the formation of several peaks that absorb at 214 nm. Mass spectrometry of the peptide materials recovered from two product peaks gave m/z values of 861 and 630, respectively. While the former product was present in hydrolysates from both PTH [1-38] and PTH [1-34], the latter product was identified only in the PTH [1-34] hydrolysate and likely corresponds to the carboxyl terminal pentapeptide DVHNF of human PTH [1-34]. These findings provide the first direct evidence that recombinant PEX possesses endopeptidase activity and that its substrate specificity may not be restricted to the putative phosphatonin, but may include other circulating hormones or perhaps bone-derived autocrine/paracrine regulatory factors that regulate renal phosphate handling. In accordance with the teachings of the present invention, PTH, and likewise PTHrP have now been found to be PEX substrates, wherein the modulation of PEX expression or activity would accordingly modulate PTH/PTHrP levels, an the inhibition of PEX expression or activity would accordingly increase PTH/PTHrP levels, thereby providing a novel treatment of bone diseases related to abnormal, namely, reduced or elevated PTH/PTHrP levels.

Discussion

To gain insight into the role of PEX in normal physiology we have cloned the human full-length cDNA and studied its expression, subcellular localization, and peptidase activity. The cloned human PEX cDNA encodes a protein whose deduced amino acid sequence is identical to the published partial (The HYP Consortium (1995) *Nature Genetics* 11, 130-136) and to the full-length sequences reported more recently (Beck, L. et al. (1997) *J. Clin. Invest.* 99, 1200-1209; Grieff, M. et al. (1997) *Biochem. Biophys. Res. Commun.* 231, 635-639; Guo, R. and Quarles, L. D. (1997) *J. Bone Miner. Res.* 12, 1009-1017). Its deduced topology is that of a type II integral membrane glycoprotein and in the present study we have provided experimental evidence to support this prediction. We have shown that PEX is glycosylated in the presence of canine microsomal membranes and partitions exclusively in the detergent phase following extraction with Triton X-114, consistent with the prediction from sequence analysis that it is an integral membrane glycoprotein. Nevertheless, the observed hydrophobic nature of PEX, need not be attributed solely to it being an integral membrane protein. Lipophilic modification is known to cause cell membrane association, presumably through hydrophobic interaction of the modifying group with the lipid bilayer. Signaled by the C-terminal tetrapeptide CRLW motif, post-translational attachment of isoprenoids via a thioether linkage to the cysteine residue would be sufficient to promote effective membrane association. Further studies will be necessary to determine if such lipid modification of PEX does indeed take place. Of interest, however, is the observation that a nonsense mutation within this motif (R747Stop) has been reported to co-segregate with HYP and is likely to be associated with an inactive PEX gene product. Finally, the localization of PEX expressed in A293 cells is also consistent with the protein being membrane-associated and corroborates the sequence-based prediction that PEX is a type II integral membrane protein with its large C-terminal hydrophilic domain in the extracellular compartment. While protein expression was detected mostly on the cell surface, in some cells the signal was also localized intracellularly. This localization of the expressed protein would indicate that a portion of PEX activity is located in a membrane-bound compartment, possibly the Golgi membranes. The Golgi localization described for ECE-1 activity in cultured endothelial cells is proposed to promote the efficient conversion of big endothelin-1 because of the co-localization and concentration of enzyme and substrate through the constitutive secretory pathway. It is possible then, that in parallel fashion, the PEX enzyme mediates both intracellular and cell-surface conversions of its putative substrate.

The finding that wild-type PEX transcripts are expressed in relative overabundance in OHO tumors poses a question in trying to understand the pathophysiology of these disorders. That is, how do we reconcile the apparently disparate observations that overexpression of PEX in OHO and loss of function in HYP patients, both lead to similar derangement in phosphate homeostasis? One of the physiological functions of PEX may well be the inactivation of a factor that normally promotes renal phosphate excretion (FIG. 9). The diagrams indicate events proposed to occur at the level of the proximal renal tubule. A putative circulating phosphaturic hormone (PHa) interacts with its renal receptor (PR) and inhibits phosphate reabsorption across the renal brush border membrane (−|) by decreasing NaPi activity. Downward arrows indicate the degree of phosphate excretion. PEX expressed predominantly in extrarenal tissues modulates the levels of circulating PHa by converting it to its inactive form (PHi).

In patients with OHO, the hyperphosphaturia that characterizes the syndrome would be the consequence of unregulated and excessive elaboration of the phosphaturic factor by the tumor. The modestly elevated PEX levels that we have documented in these tumors may arise either in response to the severe hypophosphatemia or to the abnormally high levels of the active phosphaturic factor. Yet, the increased PEX expression may not be sufficient to accommodate the increased substrate load, resulting in abnormally high circulating levels of the active phosphaturic hormone. The inactivation of PEX observed in HYP patients would similarly cause decreased turnover of this humoral phosphaturic factor and thereby lead to renal phosphate wasting.

This model is also consistent with the observation that the Hyp phenotype is neither corrected nor transferred following cross transplantation of kidneys in normal and Hyp mice. Thus, when Hyp mice are engrafted with a normal kidney, phosphaturia ensues since circulating levels of the phosphaturic agent are excessive. On the other hand, engraftment of mutant kidneys in normal mice will not affect renal tubular phosphate handling of the recipients since circulating levels of the phosphaturic substance will be normally regulated by the enzymatic activity of extrarenal wild-type PEX. Indeed, analysis of the tissue distribution of PEX mRNA by RT-PCR has confirmed its expression in extrarenal tissues and particularly bone. Our present findings and those of others (Du, L. et al. (1996) *Genomics* 36, 22-28; Beck, L. et al. (1997) *J. Clin. Invest.* 99, 1200-1209; Grieff, M. et al. (1997) *Biochem. Biophys. Res. Commun.* 231, 635-639; Guo, R. and Quarles, L. D. (1997) *J. Bone Miner. Res.* 12, 1009-1017) showing high levels of PEX expression in cells of the osteoblast lineage would be consistent with the intrinsic osteoblast defect postulated to exist in HYP patients and in Hyp mice.

Finally, although the deduced structure of PEX clearly suggests that it is a metalloprotease, until now, no peptidase activity had been ascribed to the protein. The preservation of the catalytic glutamate and histidine residues (equivalent to $E^{646}$ and $H^{711}$ of NEP; FIG. 2B) would argue for such an activity. In addition, the wide range of PEX mutations in HYP patients that align with regions required for protease activity in NEP suggests that PEX also functions as a protease. Here, for the first time, we provide experimental evidence that recombinant PEX indeed functions as an endopeptidase. Unlike NEP, however, the protein does not possess dipeptidylcarboxypeptidase activity since it lacks a residue equivalent to $R^{102}$ of NEP. Our unexpected observation that PEX effectively degrades PTH raises the question of whether circulating PTH is the putative phosphatonin. Although extracts from some OHO tumors have been reported to stimulate renal adenylate cyclase and this activity was inhibited by PTH antagonists, most studies have excluded PTH and PTH-related peptide (PTHrP) activity in OHO-associated tumors. Moreover, calcium homeostasis is generally preserved in patients with HYP. It is more likely, therefore, that the enzyme is rather promiscuous in its substrate specificity. Based on the findings of the present invention, PEX indeed modulates PTH bioavailability and bioactivity, particularly at the level of the osteoblast, as well as the hormonal and paracrine/autocrine effects of factors produced by osteoblasts involved in regulating phosphate reabsorption and osteoblast maturation and mineralization. The availability of full-length human PEX cDNA now provides us with the opportunity to study the biology of PEX, identify its substrate(s), as now shown and further described below, elucidate its role in pathological states characterized by dysregulated phosphate homeostasis, and determine its suitability as target for therapeutic intervention in the treatment of metabolic bone diseases, as concluded in the findings of the present invention.

Modulation of PTH/PTHRP Levels In-Vitro By PEX Inhibition

It is known in the art that PTH/PTHrP are powerful bone anabolic agents. It is also known that an increase in PTH/PTHrP levels will necessarily result in an increase in bone formation in the bone microenviornment.

Phosphoramidon (abbreviated herein as Pho), N-alpha-L-rhamnopyranosyloxy (hydroxyphosphinyl)-L-Leucyl-L-Tryptophan, is known in the present art as being a general potent inhibitor of neutral endopeptidases. Shirotani et al (JBC, 276(24), 21895-21901, 2001) have shown that the proteolytic activities of PHEX and homologous endopeptidases, namely, NEP, NEPLPα and NEPLPβ are inhibited by phosphoramidon.

The present application clearly shows for the first time that PEX is an endopeptidase that degrades PTH (1-34). Based on the present evidence of PEX's endopeptidase activity, it is clearly understood that PTH/PTHrP are substrates of PEX. Accordingly, since it has now been shown that PEX is an endopeptidase that cleaves PTH, and likewise PTHrP, one skilled in the present art, based on the findings of the present invention and that which is known in the present art, would clearly and reasonably understand that inhibiting the endopeptidase that degrades PTH/PTHrP, namely, inhibition of PEX, would accordingly result in an increase in PTH/PTHrP levels, and would consequently result in an increase in bone formation. Therefore, the findings of the present invention provide a novel treatment for bone disease.

It can therefore be concluded, based on the findings of the present application and that which is known in the art, that PTH/PTHrP are substrates of PEX, wherein the inhibition of PEX results in an increase in PTH/PTHrP levels, which consequently results in an increase in bone formation.

Effect of Phosphoramidon on PTHrP Expression In-Vitro and Markers of Bone Formation In-Vivo An in-vitro examination of the effects of Phosphoramidon on PTHrP expression in osteoblast cells, in-vivo examination of markers of bone formation, in particular, osteocalcin levels in-vivo was completed.

Inventors of the present application have already shown that PHEX cleaves PTH (1-34) and it was reasonably predicted that PTHrP will also be a substrate of PHEX based on homologies of PTH with PTHrP, and that which is known in the present art. Both PTH and PTHrP have already been shown to be critical bone anabolic agents and it was predicted that inhibition of PHEX could be used to increase local PTH and PTHrP levels in the bone microenvironment and hence, this would provide a novel means of treatment of metabolic bone diseases such as osteoporosis.

The aim of the present work was to determine whether inhibition of PHEX by a general endopeptidase inhibitor, such as phosphoramidon, alters PTHrP mRNA and protein expression in vitro and to assess whether these changes are reflected by increases in serum markers of bone formation, such as osteocalcin, in vivo, thereby providing evidence for the first time that the inhibition of osteoblast endopeptidases, and more preferably, inhibition of PHEX can lead to bone formation and hence provide a novel therapeutic approach for the treatment of metabolic bone diseases, such as osteoporosis.

Figure 10:
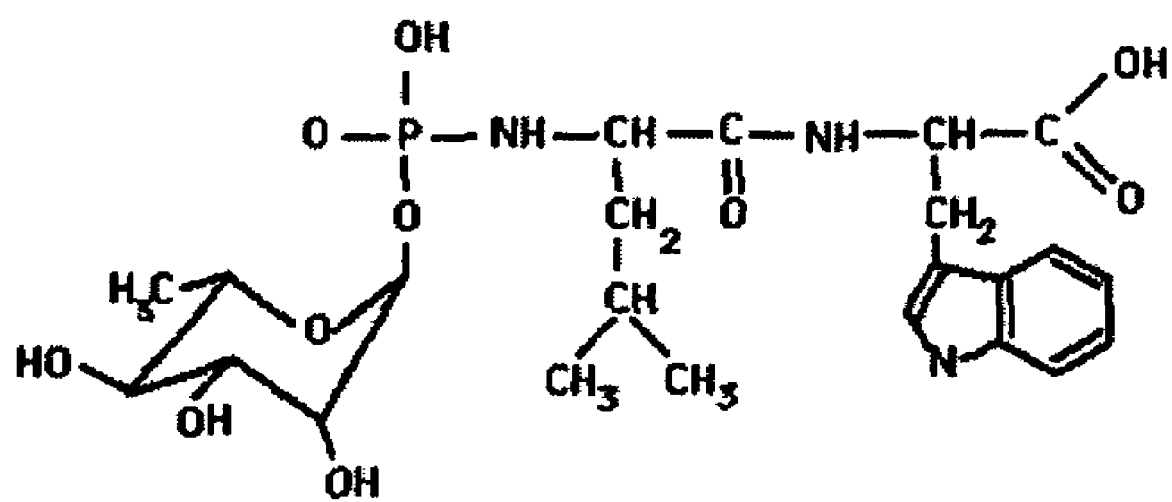
FIG. 10 illustrates the chemical structure of phosphoramidon, N-alpha-L-rhamnopyranosyloxy (hydroxyphosphinyl)-L-Leucyl-L-Tryptophan.

For these studies, inhibition of neutral endopeptidases was achieved by use of the general potent inhibitor phosphoramidon, N-alpha-L-rhamnopyranosyloxy(hydroxyphosphinyl)-L-Leucyl-L-Tryptophan (FIG. 10). Shirotani et al (JBC, 276(24), 21895-21901, 2001) have shown previously that the proteolytic activities of PHEX and homologous endopeptidases namely, NEP, NEPLPα, NEPLPβ and ECE are inhibited by phosphoramidon.

It should be noted that in accordance with the present invention, a "PEX inhibitor" is not limited to phosphoramidon, but may be any compound that inhibits the expression or enzymatic activity of PEX, where Pho is a generally known inhibitor of endopeptidase activity, and is meant to represent other endopeptidase inhibitors, and more specifically, any compound that inhibits PEX endopeptidase activity. Accordingly, a PEX inhibitor in accordance with the present invention may be selected from the group consisting of inhibitors of NEP and/or ECE and/or PEX such as phosphoramidon, phosphoramidon analogs, Zn chelators, such as O-phenanthroline, any peptides that are homologous to PTH (1-34) and contain at least one aspartate residue in their sequence, and small molecule peptidomimetic analogs of these peptides.

In-Vitro Experimental Procedure

In vitro experiments were completed where UMR-106 osteoblast cultured cells are examined with respect to PTH/PTHrP mRNA levels (using RT-PCR), and PTH/PTHrP protein levels (using an immunoradiometic assay), in the presence of PBS/Pho or PBS (control).

Stock cultures of UMR-106 osteoblast cells were maintained in DMEM supplemented with 10% fetal bovine serum (FBS), glucose (4.5 g/liter), penicillin (50 U/ml), streptomycin (50 µg/ml), glutamine (2 mM), and sodium pyruvate (1 mM) in a water-saturated atmosphere of 95% $O_2$ and 5% $CO_2$ at 37C. Cells were passaged every 3-days.

To study the effect of phosphoramidon on PTHrP expression, $2 \times 10^5$ cells were plated in 60-mm tissue culture dishes in 2 ml DMEM for 4 days with one change of medium at day 2. At day 4, cells were washed once with Hams' F-12/DMEM (1:1) without FBS and the medium was replaced with DMEM (phenol red free) supplemented as indicated above except that FBS was substituted for 10% stripped FBS and phosphoramidon (10 µM) or vehicle (PBS) were added. After 24 h, the medium was removed and kept at −80C while cells were washed twice with PBS and immediately processed for RNA extraction using the RNeasy kit (QIAGEN, Mississauga, ON) according to the manufacturer's instructions. Changes in PTHrP mRNA levels were determined by semiquantitative RT-PCR. Total RNA (2.5-5.0 µg) was reverse-transcribed with oligo(dT)$_{12-18}$ and cDNA amplified by PCR. For cDNA amplification the following sets of specific primers were used: forward: 5'-GCTACTGCATGACAAGGGCAAGTCC and reverse 5'-CATCACCCACAGGCTAGCGCCAACT. The housekeeping gene glyceraldehyde-3-phosphate dehydrogenase (G3PDH) was used as internal control. PTHrP levels in the medium were measured using an immunoradiometric assay (Diagnostic Systems Laboratories, Inc., TX.).

In-Vitro Results

Figure 11:
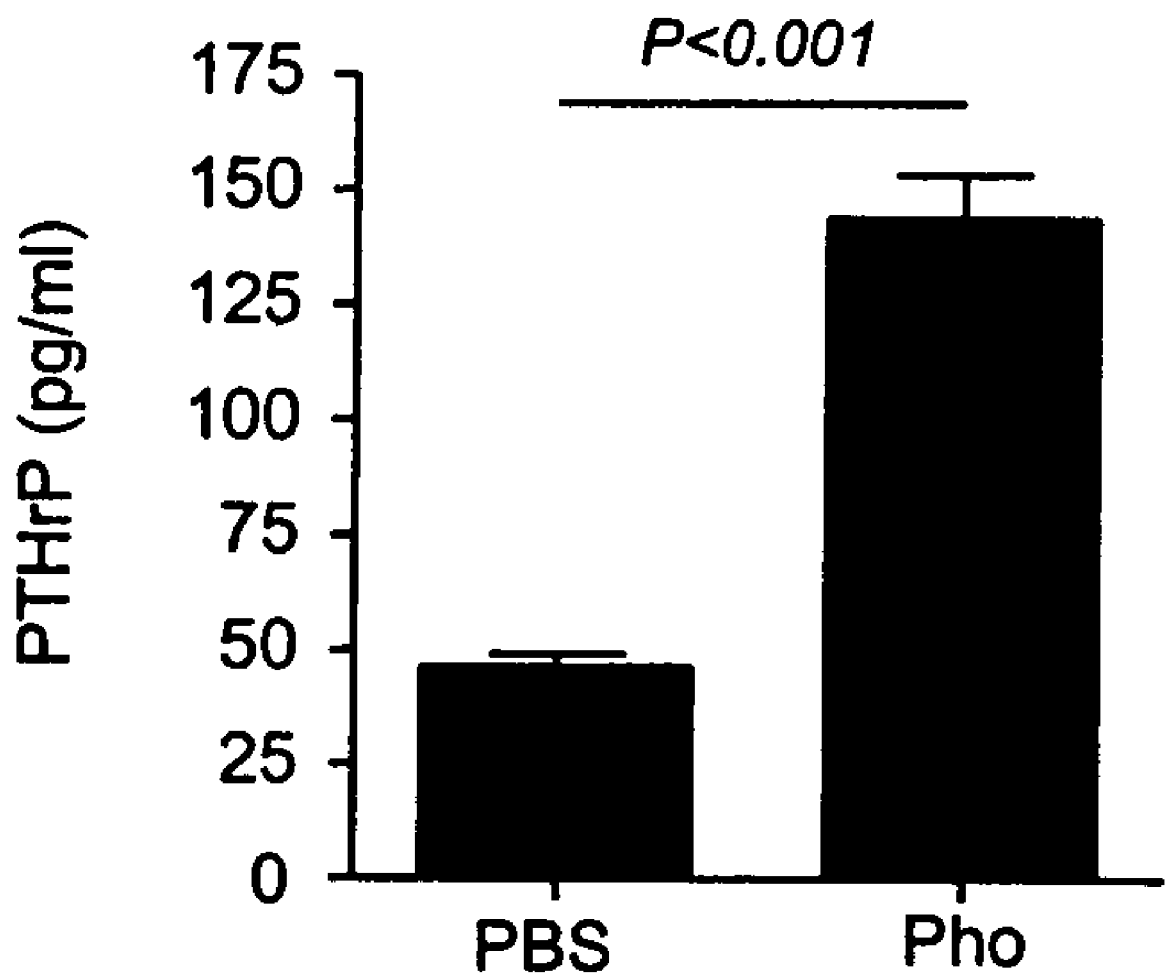
FIG. 11 illustrates in vitro PTHrP levels in UMR-106 osteoblast cells cultured in (phosphate-buffered saline (PBS) or 10 µM phosphoramidon (Pho)

Based on the in vitro results provided, and in particular, FIG. 11, there is a significant increase in PTHrP protein levels in the osteoblast culture medium. Accordingly, based on what is known with respect to PTHrP and bone formation, as described above and that which is known in the present art, this increase in PTHrP levels in the osteoblast environment indicates that bone formation should be increased, since an increase in PTHrP levels is known in the art to be reflected in an increase in bone formation. In addition to that which would be understood by one skilled in the art, based on the present findings, i.e. that an increase in PTHrP levels will translate into an increase in bone formation, additional in vivo experiments were completed to provide additional evidence that an increase in PTHrP levels results in an increase in bone formation.

It can also be noted that, based on the in-vitro results, when examining the changes in mRNA levels of PTHrP, (results not provided), it was observed that there were no significant changes in the PTHrP mRNA level in the PBS vs. Pho samples. However, the in-vitro results provided clearly show a significant change in the PTHrP protein level in the Pho samples, where Pho inhibited PEX, and allowed for increase in PTHrP protein levels. Based on these in-vitro results, where PTHrP mRNA levels were unchanged, but PTHrP protein level were increased, the increase in PTHrP protein levels in the osteoblast culture medium can be attributed to loss of post-translational processing of the PTHrP protein due to the inhibition of the PEX endopeptidase activity.

The in-vitro study confirms that Pho results in an increase in PTHrP levels, through the inhibition of PEX, where Pho's inhibition of PEX prevents PEX from acting on its substrates, namely PTH/PTHrP, as shown, thereby allowing for PTHrP levels to increase. One skilled in the art would understand that since NEP and ECE are not known to cleave PTH or PTHrP, the observed increase in PTHrP levels can be attributed to the inhibition of PEX activity; this conclusion further confirms that PTH/PTHrP are substrates of PEX. Accordingly, based on the teachings of the present invention and the experimental results provided herein, it can be concluded that the increase in PTH/PTHrP levels is due to Pho's inhibition of PEX, where PEX is inhibited from cleaving its substrates PTH/PTHrP.

Accordingly, the present invention confirms that PEX inhibitors can lead to an increase in PTH/PTHrP levels, which would in turn lead to increase in bone formation, thereby providing a novel method of treating bone disease.

As detailed above, PTHrP mRNA levels were not significantly different in cells treated with phosphoramidon compared to vehicle (PBS)-treated cells (results not shown). However, as illustrated in FIG. 11, immunoreactive PTHrP in medium conditioned by UMR-106 osteoblast cells was significantly increased (P<0.001, n=5) when cells are cultured in the presence of phosphoramidon (10 μM), compared to vehicle-treated cells. These findings indicate that inhibition of neutral endopeptidases such as NEP, ECE, and PHEX by this general potent inhibitor leads to an increase in secreted PTHrP levels that do not arise from increased PTHrP gene transcription but are likely a consequence of changes in post-translational processing of the protein because of inhibition of osteoblast endopeptidase activity. Since studies have shown that PTH and PTHrP are not substrates for NEP or ECE, the observed increase in PTHrP levels in the tissue culture medium is likely due to inhibition of PEX enzymatic activity. PTHrP is a potent endogenous bone anabolic agent. Therefore, the observed rise in PTHrP levels in the osteoblast microenvironment would consequently be expected to lead to increased bone formation. This was subsequently tested and confirmed to be true in vivo.

In-Vivo Study

It is known in the present art that osteocalcin levels are known to be directly proportional to bone formation levels, wherein an increase in osteocalcin level indicates an increase in bone formation.

The use of serum bone markers, such as osteocalcin, has been used in the clinical settings as a predictor of response to therapeutic treatment. Therefore, the maintenance of osteocalcin levels in Pho mice indicates that Pho's inhibition of NEP/ECE/PEX resulted in an increase in serum osteocalcin levels in these mice, which indicates that Pho mice experienced an increase in bone formation.

In-Vivo Experimental Procedure

Eight C57BL/6 one-month-old male mice were purchased from Charles River and housed at controlled temperature and humidity with free access to food (regular chow) and water. Following one week of acclimatization, animals were divided in two groups of 4 animals each and injected intraperitoneally daily with either phosphate-buffered saline (PBS; control group) or PBS with phosphoramidon (Sigma; 200 μg/day; phosphoramidon-treated group). Accordinlgy, two mice were injected daily for 14 days with PBS (control mice); two mice injected daily for 14 days with PBS/Pho; two mice were injected daily for 36 days with PBS (control mice) and two mice injected daily for 36 days with PBS/Pho. Serum osteocalcin levels were determined by ELISA using Rat-Mid Osteocalcin kit manufactured by Osteometer BioTech A/S (Herlev, Denmark) following 14 and 36 days of treatment.

Results of In-Vivo Experiments

Figure 12:
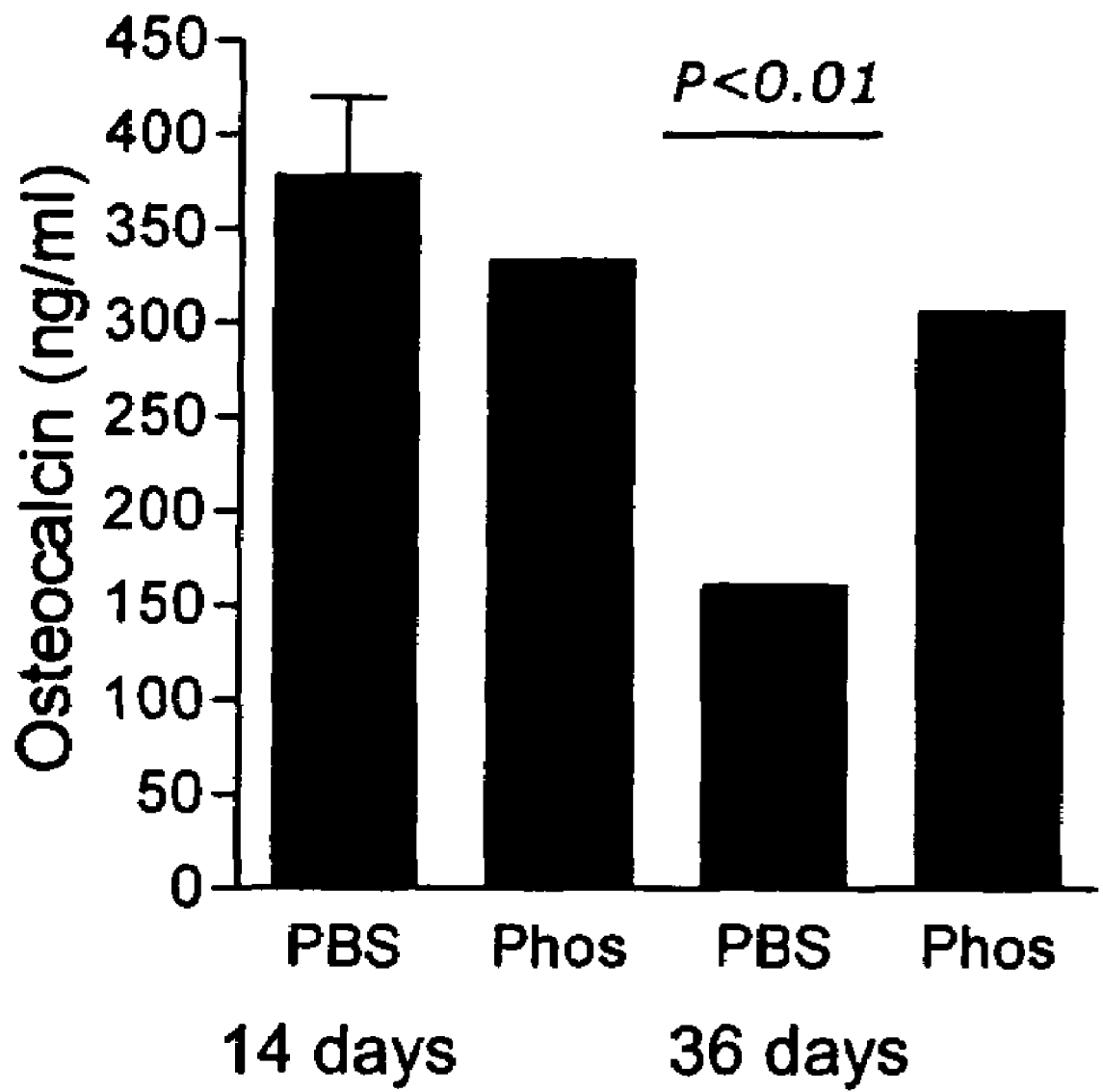
FIG. 12 illustrates in vivo serum osteocalcin levels in C57BL/6 one-month old male mice injected intraperitoneally daily with either PBS (control group) or with phosphoramidon/PBS (200 µg/day Pho) (Pho-treated group) following 14 and 36 days of treatment, as determined by ELISA using Rat-Mid Osteoclacin Kit (Osteometer BioTech A/S, Herlev, Denmark).

The in-vivo results provided, as illustrated in FIG. 12, show that osteocalcin levels were maintained in Pho treated mice at day 36, while they were decreased in the PBS control mice, as expected due to the normal aging in mice.

More specifically, as shown in FIG. 12, serum osteocalcin levels decreased from 14 to 36 days of treatment with PBS (vehicle, red bars), indicating the expected decrease in bone turnover and specifically, bone formation that normally occurs in mice with increasing age. In sharp contrast, serum osteocalcin levels remained elevated even after 36 days following daily administration of phosphoramidon (200 μg/day, blue bars), and was statistically different than levels in vehicle-treated animals (P<0.01). These findings suggest that inhibition of neutral endopeptidases such as NEP, ECE, and PEX by this general potent inhibitor and the associated increase in PTHrP levels within the skeletal microenviroment leads to an increase in serum osteocalcin level, a marker of bone formation. Therefore, inhibition of endopeptidase activity, such as PEX, on osteoblasts, offers a viable and novel therapeutic strategy in the treatment of metabolic bone disease, such as osteoporosis.

Conversely, activation of PEX enzymatic activity could be used to decrease local levels of PTH and PTHrP within the skeletal microenvironment and this could provide a viable therapeutic option in conditions such as fibrous dysplasia and osteitis fibrosa cystica in renal osteodystrophy (very frequently seen in patients with chronic renal failure), that are associated with increased PTH and PTHrP activity. That is to say, based on the results of the present invention, if it is desired to decrease bone formation, the activation of PEX would accordingly result in a decrease of PTH/PTHrP levels, and consequential a decrease in bone formation, where a decrease in osteocalcin levels would also be expected.

The present in-vivo study provides experimental evidence that the inhibition of PEX by Pho leads to a local increase in PTH/PTHrP levels, as presently shown, and therefore to an increase in serum bone formation marker, such as osteocalcin. Accordingly, inhibition of the PEX endopeptidase enzymatic activity, allows for the increase of PTH/PTHrP levels, as presently shown in the in-vitro data, thereby allowing for these powerful endogenous bone forming agents to cause an increase in bone formation, as evidenced by an increase in osteocalcin levels, as shown in the present in-vivo data.

These results allow one skilled in the art to conclude that the inhibition of PEX, by Pho, results in an increase in bone formation, as evidenced by the maintenance of osteocalcin levels in aging mice. Therefore, the present invention is further confirmed to provide a novel method of treating bone disease through the inhibition of PEX activity.

Accordingly, the present invention provides a method of treating bone disease by the inhibition or modulation of PEX, wherein any compounds that bind to PEX and modulate or inhibit the enzymatic activity of PEX, are compounds that can be used for the treatment of metabolic bone disease. For example, any compound that prevents PEX from acting on its substrates, and more preferably from acting on PTH/PTHrP is a compound that can be used in the treatment of metabolic bone disease, since, based on the findings and teachings of the present invention, said compound would allow for an increase in PTH/PTHrP levels, through the inhibition of PEX, thereby leading to an increase in bone formation.

Accordingly, the present invention also provides a method of modulating PTH/PTHrP levels, wherein the modulation of PTH/PTHrP levels comprises the modulation of PEX, and more preferably the inhibition of PEX. The present invention thereby provides a method of treating bone disease through the inhibition of PEX.

It has been clearly shown that PEX is the endopeptidase that cleaves PTH, and likewise PTHrP, wherein the inhibition of PEX is shown to result in an increase in PTHrP levels in osteoblast microenviornment, and consequently in an increase in bone formation. Therefore, the present invention clearly provides that the inhibition of PEX and other osteoblast endopeptidases results in an increase in bone formation, to therefore provide a new treatment method for bone disease, and more preferably osteoporosis.

Accordingly, the present invention provides a method for treating metabolic bone disease, wherein the modulation of PTH and/or PTHrP is further defined as being through the modulation of PEX, as supported by the teachings and experimental evidence of the present application, where it is clearly shown for the first time, with enabling evidence, that PEX is the modulating compound that modulates PTH and/or PTHrP levels, and where the modulation of PEX, by a PEX-binding substrate affects or modulates the enzymatic activity of PEX, to effectively elicit the modulation of PTH and/or PTHrP levels, thereby providing a method of treating a metabolic bone disease.

The present application further relates to a mechanism of treating a metabolic bone disease by the modulation of PTH and/or PTHrP levels through PEX. As is clearly described and supported with experimental evidence, an underlying mechanism for such PTH/PTHrP modulation is the alteration in the bone micro-environmental concentration of critical bone anabolic agents, namely PTH and PTHrP, which are shown for the first time to be modulated by PEX enzymatic activity.

The teachings of the present application clearly provide evidence of the modulation of PTH/PTHrP by PEX. More specifically, the present application provides evidence that PEX is the endopeptidase compound that is shown to cleave PTH and likewise PTHrP. More specifically, PEX is shown to be an endopeptidase that cleaves PTH(1-34), PTH(1-38), and, as would be understood by one skilled in the present art, likewise would cleave PTHrP. Accordingly, the modulation of PEX enzymatic activity therefore provides a means of modulating PTH/PTHrP levels, wherein this means of modulation has not been provided in the prior art, and is clearly described and enabled by the teachings of the present invention.

The present invention also provides that PEX has homology with NEP (neprilysin), thereby providing evidence that PEX is an endopeptidase and a member of the endopeptidase family, which also comprises ECE-1 and Kell antigen (as noted above, and illustrated in FIG. 2B). It should also be noted that in addition to the above points, the present invention describes and provides enabling evidence that PEX is the compound, i.e. the endopeptidase compound that modulates PTH/PTHrP, as clearly described above. In view of the teachings of the present description and the evidence provided therein, a method of treating a metabolic bone disease, wherein PEX is shown to be a modulator of PTH/PTHrP levels, and wherein the modulation of PEX effectively modulates PTH/PTHrP levels is embodied in the present invention. Accordingly, based on the teachings of the present invention, and on the knowledge of one skilled in the art, the design of PEX inhibitors/modulators for the subsequent modulation of PTH/PTHrP levels may be accomplished, wherein any PEX-binding substrate, such as any known inhibitors of NEP, for example, phosphoramidon, which may affect PEX enzymatic activity may be used to modulate PEX activity, which would in turn modulate PTH/PTHrP levels and hence modulate bone formation and bone breakdown.

The present invention clearly provides one skilled in the art with a means for the identification or design of PEX inhibitors for the modulation of PTH/PTHrP levels, wherein said PEX modulators are PEX binding substrates that modulate or affect PEX enzymatic activity. For example, one skilled in the art would understand that an examination of PTH breakdown fragments allows for the determination of the cleavage sites of the PEX substrate, namely the cleavage sites of PTH/PTHrP, so as to thereby lead one skilled in the art to readily design PEX inhibiting compounds. Moreover, the present application clearly describes the interactions between PEX-PTH, and likewise, clearly describes the mechanisms and interactions between PEX-PTHrP. It should also be noted that the present invention also provides for the use of inhibitors to PEX related enzymes. For example, the present invention also provides for the use of inhibitors to PEX related enzymes. More specifically, since Neprilysin (NEP) is homologous to PEX, wherein a description of the structural relation of PEX to NEP is provided, and wherein NEP, like PEX is an endopeptidase, it would be understood, that an NEP inhibiting compound, such as phosphoramidon, could likewise be a PEX inhibiting compound, as supported by the present experimental results provided. Accordingly, the present invention contemplates that known NEP inhibitors may additionally be PEX inhibitors. Accordingly, in light of what is known in the prior art, and what is now provided in the teachings of the present application, where PEX is shown to be the PTH/PTHrP modulating compound, it is understood and embodied in the present invention that any compound that modulates PEX, i.e. a PEX binding substrate that modulates or affects PEX expression or PEX enzymatic activity will accordingly modulate PTH/PTHrP levels.

As noted above, the present application additionally teaches that PEX has homology to members of membrane bound metalloendopeptidase enzymes, such as ECE-1 and Kell antigen. PEX has also been shown to require zinc (Zn) in the allosteric site for catalytic proteolytic activity. Accordingly, based on the teachings of the present invention and the evidence provided therein, one skilled in the art would recognize metal chelators, such as 0-phenanthroline, to be a potential PEX inhibitor for the development of novel agents to treat metabolic bone disease based on the mechanisms provided in the present application.

Furthermore, the present application clearly describes the modulation of PTH/PTHrP levels, as illustrated in FIG. 11, and an increase in bone formation in-vivo as evidenced by serum bone marker osteocalcin levels, as illustrated in FIG. 12. The present application therefore provides for the modulation of PTH/PTHrP levels through PEX, and accordingly the modulation of PEX. Moreover, the present invention also teaches and describes the homology between PEX and NEP, wherein said homology would allow and provide sufficient instruction for one skilled in the art to formulate a therapeutically effective dose of a known inhibitor of NEP, such as phosphoramidon, for the use in the modulation or inhibition of PEX so as to accordingly modulate PEX and subsequently modulate PTH/PTHrP levels so as to promote bone formation and to treat metabolic bone disease. The present application therefore relates to a method of treating metabolic bone disease by the modulation of PTH/PTHrP levels.

Accordingly, the present invention sufficiently describes a method for modulating PTH/PTHrP levels for the treatment of metabolic bone disease wherein said modulation of PTH and/or PTHrP is clearly described as a result of the modulation of PEX. The present application also provides the use a compound for the modulation of PTH and/or PTHrP levels wherein said compound is a compound that modulates the enzymatic activity of the PEX.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I/We claim:

1. A method for treating osteoporosis in a patient, said method comprising administering to said patient phosphoramidon or a composition comprising phosphoramidon as active agent, in an amount effective to inhibit PEX expression and/or PEX enzymatic activity.

2. The method according to claim 1, wherein said phosphoramidon or a composition comprising phosphoramidon as active agent is administered in an amount effective to increase PTH and/or PTHrP levels in osteoblast microenvironment.

3. A method for increasing bone formation in an osteoporotic patient, said method comprising administering to said patient phosphoramidon or a composition comprising phosphoramidon as active agent in an amount effective to increase PTH and/or PTHrP levels in osteoblast microenvironment.

* * * * *